US 7,011,838 B2
Mar. 14, 2006

(12) United States Patent
Otaka et al.

(54) MALONONITRILE COMPOUNDS AND THEIR USE AS PESTICIDES

(75) Inventors: Ken Otaka, Toyonaka (JP); Daisuke Oohira, Minoo (JP); Satoshi Okada, Takarazuka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 111 days.

(21) Appl. No.: 10/477,117

(22) PCT Filed: May 8, 2002

(86) PCT No.: PCT/JP02/04449

§ 371 (c)(1),
(2), (4) Date: Nov. 7, 2003

(87) PCT Pub. No.: WO02/090320

PCT Pub. Date: Nov. 14, 2002

(65) Prior Publication Data

US 2004/0138065 A1     Jul. 15, 2004

(30) Foreign Application Priority Data

May 9, 2001    (JP) ............................. 2001-138331

(51) Int. Cl.
*A01N 25/00* (2006.01)
*A01N 43/26* (2006.01)
*C07C 255/00* (2006.01)

(52) U.S. Cl. .................. 424/405; 504/296; 558/388
(58) Field of Classification Search ............... 558/388; 504/296; 424/405
See application file for complete search history.

(56) References Cited

U.S. PATENT DOCUMENTS 4,000,314 A    12/1976  Drabek
2004/0142821 A1 *  7/2004  Otaka et al. ............... 504/296

FOREIGN PATENT DOCUMENTS

| JP | 6-256278 | 9/1994 |
| JP | 10-29966 | 2/1998 |
| WO | 98 35935 | 8/1998 |

OTHER PUBLICATIONS

Hiroyuki Nakamura et al., "Palladium-catalyzed cyanoallylation of activated olefins", Tetrahedron Letters, vol. 41, pp. 2911-2914, 2000.
Hiroyuki Nakamura et al., "Palladium-Catalyzed Alkoxyallylation of Activated Olefins", J. Am. Chem. Soc., vol. 120, pp. 6838-6839, 1998.
Reinhard Brückner et al., "Substitutions and Dehydrogenations by 2,2-Bis(Triflurormethyl)-Ethylene-1,1-Dicarbonitrile Via Hydride Abstraction", Tetrahedron Letters, vol. 32, No. 16, pp. 1875-1878, 1991.

Kazuhiko Mizuno et al., "Regioselective Double Vicinal Carbon-Carbon Bond-Forming Reactions of Electron-Deficient Alkenes by Use of Allylic Stannanes and Organoiodo Compounds", J. Am. Chem. Soc., vol. 110, pp. 1288-1290, 1988.
Steven D. Barker et al., "Radical and Ionic Nucleophilic Substitution Reactions on α-Alkyl-γ-(p-nitrophenyl)allyl Derivatives", Aust. J. Chem., vol. 36, pp. 527-544, 1983.
Richard Sommer et al., "Synthesen mit N-Trialkylstannylketerniminen", Justus Liebigs Ann. Chem., vol. 718, pp. 11-23, 1968.
A. D. Josey et al., "Trifluoromethylmalononitrile. The Reaction of 1,1-Dichloro-2,2-dicyanoethylene with Argentous Fluoride", J. Org. Chem., vol. 32, pp. 1941-1944, 1967.
Dr. R. Sommer et al., "Syntheses with N-Stannylketenimines and Ketene Ethyl Stannyl Acetals", Angew. Chem., Int. Ed. Eng., vol. 5, p. 515, 1966.
W. Russell Bowman et al., "Radical cyclisation onto nitriles", Tetrahedron Letters, vol. 41, pp. 8989-8994, 2000.
Roger L. Xie et al., "The synthesis of highly functionalized seven-membered allyl ethers using palladium-catalyzed alkoxyallylation of activated olefins and ring-closing olefin metathesis", Tetrahedron Letters, vol. 41, pp. 10167-10170, 2000.

(Continued)

*Primary Examiner*—Johann Richter
*Assistant Examiner*—Ebenezer Sackey
(74) *Attorney, Agent, or Firm*—Wenderoth, Lind & Ponack, L.L.P.

(57) ABSTRACT

The present invention relates to malononitrile compounds of formula (Y)

wherein $R^1$ and $R^2$ are the same or different and independently $C_1$–$C_5$ (halo)alkyl, $C_1$–$C_5$ (halo)alkyloxy, $C_2$–$C_5$ (halo)alkenyl, $C_2$–$C_5$ (halo)alkynyl, hydrogen, or cyano; $R^3$ is $C_1$–$C_3$ haloalkyl, $C_2$–$C_4$ haloalkenyl, or $C_2$–$C_4$ haloalkynyl; m is an integer of 1 to 3; $R^5$ is halogen, cyano, nitro, $C_1$–$C_4$ (halo)alkyl, or the like; n is an integer of 0 to 4, with the proviso that when n is 2 or more, then $R^5$'s are the same or different from each other; $R^6$ is hydrogen, halogen, cyano, nitro, $C_1$–$C_4$ (halo)alkyl, or the like; as well as pesticide compositions containing these compounds as active ingredients. The present invention makes it possible to effectively control pests such as insect pests, acarine pests, and nematode pests.

9 Claims, No Drawings

OTHER PUBLICATIONS

Niclas Solin et al., "Control of the Regioselectivity in Catalytic Transformations Involving Amphiphilic Bis-allylpalladium Intermediates: Mechanism and Synthetic Applications", J. Org. Chem., vol. 66, pp. 1686-1693, 2001.

Isao Kadota et al., "Palladium/Acetic Acid Catalyzed Allylation of Some Pronucleophiles with Simple Alkynes", J. Am. Chem. Soc., vol. 120, pp. 10262-10263, 1998.

Jae-Goo Shim et al., "Palladium Catalyzed Regioselective β-Acetonation-α-Allylation of Activated Olefins in One Shot", J. Org. Chem., vol. 63, pp. 8470-8474, 1998.

Hiroyuki Nakamura et al., "Amphiphilic Catalytic Allylating Reagent, Bis-π-allylpalladium Complex", J. Am. Chem. Soc., vol. 119, pp. 8113-8114, 1997.

Bèatrice Quiclet-Sire et al., "New Radical Allylation Reaction", J. Am. Chem. Soc., vol. 118, pp. 1209-1210, 1996.

Bruce D. Jacobs et al., "Steric and Electronic Limitations of the $S_{RN}1$ Reaction Between p-Nitrobenzylic Substrates and Tertiary Carbanions", Tetrahedron Letters, vol. 26, No. 29, pp. 3495-3498, 1985.

Steven D. Barker et al., Nucleophilic Substitution Reactions in m-Nitrobenzylic Substrates, Aust. J. Chem., vol. 36, pp. 81-95, 1983.

Werner Barbe et al., "Die thermische Stabilität 2,2-disubstituierter Malononitrile", Chem. Ber., vol. 116, pp. 1058-1069, 1983.

Richard C. Cookson et al. "The Wavelength- and Solvent-dependent Photochemistry of 1,1-Dicyano-2-methyl-4-phenylbut-1-ene; Reaction from Two Excited States", J. Chem. Soc., Perkin Trans., vol. 2, pp. 774-781, 1981.

Roy A. Swaringen, Jr., et al., "Reaction of Orthoformates with Acidic Methines", J. Org. Chem., vol. 44, pp. 4825-4829, 1979.

* cited by examiner

MALONONITRILE COMPOUNDS AND THEIR USE AS PESTICIDES

TECHNICAL FIELD

The present invention relates to malononitrile compounds and their use as pesticide compositions.

BACKGROUND ART

Against pests such as insect pests, acarine pests, and nematode pests, various pesticide compositions have been used so far for their control. The conditions of pesticide compositions required have drastically been changed, including the care of their effects on the environment and the acquisition of drug resistance by pests to be controlled. Under such circumstances, there have been great demands for the development of new pesticide compositions.

DISCLOSURE OF INVENTION

The present inventors have extensively studied to find compounds having excellent pest controlling activity. As a result, they have found that the malononitrile compounds of formula (Y) as depicted below have excellent controlling activity against pests such as insect pests, acarine pests, and nematode pests, thereby reaching the present invention.

That is, the present invention provides malononitrile compounds of formula (Y):

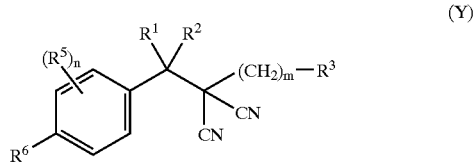

(hereinafter referred to as the present compound(s))

wherein $R^1$ and $R^2$ are the same or different and independently $C_1$–$C_5$ (halo)alkyl, $C_1$–$C_5$ (halo)alkyloxy, $C_2$–$C_5$ (halo)alkenyl, $C_2$–$C_5$ (halo)alkynyl, hydrogen, or cyano;

$R^3$ is $C_1$–$C_3$ haloalkyl, $C_2$–$C_4$ haloalkenyl, or $C_2$–$C_4$ haloalkynyl;

m is an integer of 1 to 3;

$R^5$ is halogen, cyano, nitro, $C_1$–$C_4$ (halo)alkyl, $C_2$–$C_4$ (halo)alkenyl, $C_2$–$C_4$ (halo)alkynyl, $C_1$–$C_4$ (halo)alkyloxy, $C_1$–$C_4$ (halo)alkylthio, $C_1$–$C_4$ (halo)alkylsulfinyl, $C_1$–$C_4$ (halo)alkylsulfonyl, $C_1$–$C_4$ (halo)alkylcarbonyl, $C_1$–$C_4$ (halo)alkyloxycarbonyl, $C_1$–$C_4$ (halo)alkylcarbonyloxy, benzyloxy, phenyloxy, or phenylthio, in which the phenyloxy and phenylthio groups may optionally be substituted with halogen or $C_1$–$C_3$ alkyl;

n is an integer of 0 to 4;

$R^6$ is hydrogen, halogen, cyano, nitro, $C_1$–$C_4$ (halo)alkyl, $C_2$–$C_4$ (halo)alkenyl, $C_2$–$C_4$ (halo)alkynyl, $C_1$–$C_4$ (halo)alkyloxy, $C_1$–$C_4$ (halo)alkylthio, $C_1$–$C_4$ (halo)alkylsulfinyl, $C_1$–$C_4$ (halo)alkylsulfonyl, $C_1$–$C_4$ (halo)alkylcarbonyl, $C_1$–$C_4$ (halo)alkyloxycarbonyl, $C_1$–$C_4$ (halo)alkylcarbonyloxy, benzyloxy, phenyloxy, or phenylthio, in which the phenyloxy and phenylthio groups may optionally be substituted with halogen or $C_1$–$C_3$ alkyl;

with the proviso that when n is 2 or more, then $R^5$'s are the same or different from each other.

The present invention also provides use of the present compounds as a pesticide; pesticide compositions comprising the present compounds as active ingredients; and a pest controlling method comprising applying the present compounds to pests or habitats of pests.

MODE FOR CARRYING OUT THE INVENTION

In the definition of substituents as used herein, each group has the following meaning:

The (halo)alkyl group refers to alkyl optionally substituted with halogen for one or more than one hydrogen atoms.

The (halo)alkyloxy group refers to alkyloxy optionally substituted with halogen for one or more than one hydrogen atoms.

The (halo)alkenyl group refers to alkenyl optionally substituted with halogen for one or more than one hydrogen atoms.

The (halo)alkynyl group refers to alkynyl optionally substituted with halogen for one or more than one hydrogen atoms.

The (halo)alkylthio group refers to alkylthio optionally substituted with halogen for one or more than one hydrogen atoms.

The (halo)alkylsulfinyl group refers to alkylsulfinyl optionally substituted with halogen for one or more than one hydrogen atoms.

The (halo)alkylsulfonyl group refers to alkylsulfonyl optionally substituted with halogen for one or more than one hydrogen atoms.

The (halo)alkylcarbonyl group refers to alkylcarbonyl optionally substituted with halogen for one or more than one hydrogen atoms.

The (halo)alkyloxycarbonyl group refers to alkyloxycarbonyl optionally substituted with halogen for one or more than one hydrogen atoms.

The (halo)alkylcarbonyloxy group refers to alkylcarbonyloxy optionally substituted with halogen for one or more than one hydrogen atoms.

The haloalkyl group refers to alkyl substituted with halogen for at least one or more hydrogen atoms.

The haloalkenyl group refers to alkenyl substituted with halogen for at least one or more hydrogen atoms.

The haloalkynyl group refers to alkynyl substituted with halogen for at least one or more hydrogen atoms.

The term "C1–C10" or the like refers to number of carbon atoms constituting the alkyl, alkenyl, or alkynyl group in each substituent. For example, $C_1$–$C_4$ (halo)alkylcarbonyl means alkylcarbonyl optionally substituted with halogen for one or more hydrogen atoms wherein the alkyl part is constituted by $C_1$–$C_4$ carbon atoms.

In the present compounds, each group includes specific ones as listed below:

The $C_1$–$C_5$ (halo)alkyl group represented by $R^1$ or $R^2$ may include methyl, ethyl, propyl, 1-methylethyl, 1,1-dimethylethyl, 2,2-dimethylpropyl, chloromethyl, fluoromethyl, difluoromethyl, trifluoromethyl, 2,2,2-trifluoroethyl, and 1,1,2,2-tetrafluoroethyl.

The $C_1$–$C_5$ (halo)alkyloxy group represented by $R^1$ or $R^2$ may include methoxy, ethoxy, 1-methylethoxy, trifluoromethoxy, difluoromethoxy, 2,2,2-trifluoroethoxy, and 1,1,2,2-tetrafluoroethoxy.

The $C_2$–$C_5$ (halo)alkenyl group represented by $R^1$ or $R^2$ may include vinyl, 1-propenyl, 2-propenyl, 2,2-difluorovinyl, and 1,2,2-trifluorovinyl.

The $C_2$–$C_5$ (halo)alkynyl group represented by $R^1$ or $R^2$ may include ethynyl, 1-propynyl, 2-propynyl and 3,3,3-trifluoro-1-propynyl.

The $C_1$–$C_3$ haloalkyl group represented by $R^3$ may include fluoromethyl, chloromethyl, difluoromethyl, dichloromethyl, trifluoromethyl, trichloromethyl, 1,1-difluoroethyl, pentafluoroethyl, 1,1-difluoropropyl, heptafluoropropyl, 2,2,2-trifluoroethyl, 3,3,3-trifluoropropyl, and 1,1,2,2-tetrafluoroethyl.

The $C_2$–$C_4$ haloalkenyl group represented by $R^3$ may include 1-chlorovinyl, 2-chlorovinyl, 1-fluorovinyl, 2-fluorovinyl, 2,2-dichlorovinyl, 2,2-dibromovinyl, 2,2-difluorovinyl, 1,2,2-trifluorovinyl, 1-(trifluoromethyl)vinyl, 3,3,3-trifluoro-1-propenyl, 2,3,3,3-tetrafluoro-1-propenyl, 1,2,3,3,3-pentafluoro-1-propenyl, 3,3-difluoro-2-propenyl, 2,3,3-trifluoro-2-propenyl, and 3,4,4-trifluoro-3-butenyl.

The $C_2$–$C_4$ haloalkynyl group represented by $R^3$ may include 3-chloro-2-propynyl and 3,3,3-trifluoro-1-propynyl.

The halogen atom represented by $R^5$ or $R^6$ may include fluorine, chlorine, bromine, and iodine.

The $C_1$–$C_4$ (halo)alkyl group represented by $R^5$ or $R^6$ may include methyl, ethyl, propyl, 1-methylethyl, 1,1-dimethylethyl, trifluoromethyl, pentafluoroethyl, 3,3,3-trifluoroethyl, and 1,1,2,2-tetrafluoroethoxy.

The $C_2$–$C_4$ (halo)alkenyl group represented by $R^5$ or $R^6$ may include vinyl, 1-propenyl, 2-propenyl and 2,2-difluorovinyl.

The $C_2$–$C_4$ (halo)alkynyl group represented by $R^5$ or $R^6$ may include ethynyl, 1-propynyl, 2-propynyl and 3,3,3-trifluoro-1-propynyl.

The $C_1$–$C_4$ (halo)alkyloxy group represented by $R^5$ or $R^6$ may include methoxy, ethoxy, trifluoromethoxy, bromodifluoromethoxy, difluoromethoxy, chlorodifluoromethoxy, pentafluoroethoxy, 2,2,2-trifluoroethoxy, and 1,1,2,2-tetrafluoroethoxy.

The $C_1$–$C_4$ (halo)alkylthio group represented by $R^5$ or $R^6$ may include methylthio, trifluoromethylthio, 2,2,2-trifluoroethylthio, and 1,1,2,2-tetrafluoroethylthio.

The $C_1$–$C_4$ (halo)alkylsulfinyl group represented by $R^5$ or $R^6$ may include methylsulfinyl and trifluoromethylsulfinyl.

The $C_1$–$C_4$ (halo)alkylsulfonyl group represented by $R^5$ or $R^6$ may include methylsulfonyl and trifluoromethylsulfonyl.

The $C_1$–$C_4$ (halo)alkylcarbonyl group represented by $R^5$ or $R^6$ may include acetyl and trifluoroacetyl.

The $C_1$–$C_4$ (halo)alkyloxycarbonyl group represented by $R^5$ or $R^6$ may include methoxycarbonyl and 2,2,2-trifluoroethoxycarbonyl.

The $C_1$–$C_4$ (halo)alkylcarbonyloxy group represented by $R^5$ or $R^6$ may include acetyloxy, propionyloxy, and trifluoroacetyloxy.

The phenyloxy group optionally substituted with halogen or $C_1$–$C_3$ alkyl, which is represented by $R^5$ or $R^6$, may include phenoxy, p-methylphenoxy, m-methylphenoxy, and p-chlorophenoxy.

The phenylthio group optionally substituted with halogen or $C_1$–$C_3$ alkyl, which is represented by $R^5$ or $R^6$, may include phenylthio, p-methylphenylthio, m-methylphenylthio, and p-chlorophenylthio.

The embodiments of the present invention may include the following compounds:

The malononitrile compounds of formula (Y) wherein $R^1$ is hydrogen, and $R^2$ is $C_1$–$C_5$ (halo)alkyl, $C_2$–$C_5$ (halo)alkenyl, or hydrogen;

The malononitrile compounds of formula (Y) wherein $R^1$ and $R^2$ are both hydrogen;

The malononitrile compounds of formula (Y) wherein $R^3$ is $C_1$–$C_3$ fluoroalkyl or $C_2$–$C_4$ fluoroalkenyl;

The malononitrile compounds of formula (Y) wherein $R^5$ is halogen, n is an integer of 0 to 2;

The malononitrile compounds of formula (Y) wherein $R^6$ is halogen, cyano, nitro, $C_1$–$C_4$ haloalkyl, $C_1$–$C_4$ haloalkyloxy, or $C_1$–$C_4$ haloalkylthio;

The malononitrile compounds of formula (Y) wherein $R^5$ is halogen, n is an integer of 0 to 2, and $R^6$ is halogen, cyano, nitro, $C_1$–$C_4$ haloalkyl, $C_1$–$C_4$ haloalkyloxy, or $C_1$–$C_4$ haloalkylthio;

The malononitrile compounds of formula (Y) wherein $R^3$ is $C_1$–$C_3$ fluoroalkyl or $C_2$–$C_4$ fluoroalkenyl, $R^5$ is halogen, n is an integer of 0 to 2, and $R^6$ is halogen, cyano, nitro, $C_1$–$C_4$ (halo)alkyl, $C_1$–$C_4$ (halo)alkyloxy, or $C_1$–$C_4$ (halo)alkylthio;

The malononitrile compounds of formula (Y) wherein $R^1$ and $R^2$ are the same or different and independently $C_1$–$C_3$ (halo)alkyl, $C_1$–$C_3$ (halo)alkyloxy, $C_2$–$C_4$ (halo)alkenyl, $C_2$–$C_4$ (halo)alkynyl, hydrogen, or cyano; $R^5$ and $R^6$ are the same or different and independently halogen, cyano, nitro, $C_1$–$C_3$ haloalkyl, $C_1$–$C_3$ haloalkyloxy, $C_1$–$C_3$, (halo)alkylthio, $C_1$–$C_3$ (halo)alkylsulfinyl, $C_1$–$C_3$ (halo)alkylsulfonyl, $C_1$–$C_3$ (halo)alkylcarbonyl, or $C_1$–$C_3$ haloalkyloxycarbonyl;

The malononitrile compounds of formula (Y) wherein $R^1$ is hydrogen, $R^2$ is $C_1$–$C_5$ (halo)alkyl, $C_2$–$C_5$ (halo)alkenyl, or hydrogen, $R^3$ is $C_1$–$C_3$ fluoroalkyl or $C_2$–$C_4$ fluoroalkenyl, $R^5$ is halogen, n is an integer of 0 to 2, and $R^6$ is halogen, cyano, nitro, $C_1$–$C_4$ (halo)alkyl, $C_1$–$C_4$ (halo)alkyloxy, or $C_1$–$C_4$ (halo)alkylthio;

The malononitrile compounds of formula (Y) wherein $R^3$ is 1,2,2-trifluorovinyl, m is 2, and $R^6$ is trifluoromethyl;

The malononitrile compounds of formula (Y) wherein $R^3$ is 1,2,2-trifluorovinyl, m is 2, and $R^6$ is difluoromethoxy;

The malononitrile compounds of formula (Y) wherein $R^3$ is 1,2,2-trifluorovinyl, m is 2, and $R^6$ is trifluoromethoxy;

The malononitrile compounds of formula (Y) wherein $R^3$ is 1,2,2-trifluorovinyl, m is 2, and $R^6$ is trifluoromethylthio;

The malononitrile compounds of formula (Y) wherein $R^3$ is 1,2,2-trifluorovinyl, m is 2, and $R^6$ is 1,1,2,2-tetrafluoroethoxy;

The malononitrile compounds of formula (Y) wherein $R^3$ is 1,2,2-trifluorovinyl, m is 2, and $R^6$ is chlorine;

The malononitrile compounds of formula (Y) wherein $R^3$ is 1,2,2-trifluorovinyl, m is 2, and $R^6$ is bromine;

The malononitrile compounds of formula (Y) wherein $R^3$ is 1,2,2-trifluorovinyl, m is 2, and $R^6$ is fluorine;

The malononitrile compounds of formula (Y) wherein $R^3$ is 1,2,2-trifluorovinyl, m is 2, and $R^6$ is cyano;

The malononitrile compounds of formula (Y) wherein $R^3$ is 1,2,2-trifluorovinyl, m is 2, and $R^6$ is nitro;

The malononitrile compounds of formula (Y) wherein $R^3$ is trifluoromethyl, m is 2, and $R^6$ is trifluoromethyl;

The malononitrile compounds of formula (Y) wherein $R^3$ is trifluoromethyl, m is 2, and $R^6$ is difluoromethoxy;

The malononitrile compounds of formula (Y) wherein $R^3$ is trifluoromethyl, m is 2, and $R^6$ is trifluoromethoxy;

The malononitrile compounds of formula (Y) wherein $R^3$ is trifluoromethyl, m is 2, and $R^6$ is trifluoromethylthio;

The malononitrile compounds of formula (Y) wherein $R^3$ is trifluoromethyl, m is 2, and $R^6$ is 1,1,2,2-tetrafluoroethoxy;

The malononitrile compounds of formula (Y) wherein $R^3$ is trifluoromethyl, m is 2, and $R^6$ is chlorine;

The malononitrile compounds of formula (Y) wherein $R^3$ is trifluoromethyl, m is 2, and $R^6$ is bromine;

The malononitrile compounds of formula (Y) wherein $R^3$ is trifluoromethyl, m is 2, and $R^6$ is fluorine;

The malononitrile compounds of formula (Y) wherein $R^3$ is trifluoromethyl, m is 2, and $R^6$ is cyano;
The malononitrile compounds of formula (Y) wherein $R^3$ is trifluoromethyl, m is 2, and $R^6$ is nitro;
The malononitrile compounds of formula (Y) wherein $R^3$ is pentafluoroethyl, m is 2, and $R^6$ is trifluoromethyl;
The malononitrile compounds of formula (Y) wherein $R^3$ is pentafluoroethyl, m is 2, and $R^6$ is difluoromethoxy;
The malononitrile compounds of formula (Y) wherein $R^3$ is pentafluoroethyl, m is 2, and $R^6$ is trifluoromethoxy;
The malononitrile compounds of formula (Y) wherein $R^3$ is pentafluoroethyl, m is 2, and $R^6$ is trifluoromethylthio;
The malononitrile compounds of formula (Y) wherein $R^3$ is pentafluoroethyl, m is 2, and $R^6$ is 1,1,2,2-tetrafluoroethoxy;
The malononitrile compounds of formula (Y) wherein $R^3$ is pentafluoroethyl, m is 2, and $R^6$ is chlorine;
The malononitrile compounds of formula (Y) wherein $R^3$ is pentafluoroethyl, m is 2, and $R^6$ is bromine;
The malononitrile compounds of formula (Y) wherein $R^3$ is pentafluoroethyl, m is 2, and $R^6$ is fluorine;
The malononitrile compounds of formula (Y) wherein $R^3$ is pentafluoroethyl, m is 2, and $R^6$ is cyano;
The malononitrile compounds of formula (Y) wherein $R^3$ is pentafluoroethyl, m is 2, and $R^6$ is nitro;
The malononitrile compounds of formula (Y) wherein $R^3$ is trifluoromethyl, m is 1, and $R^6$ is trifluoromethyl;
The malononitrile compounds of formula (Y) wherein $R^3$ is trifluoromethyl, m is 1, and $R^6$ is trifluoromethoxy;
The malononitrile compounds of formula (Y) wherein $R^3$ is trifluoromethyl, m is 1, and $R^6$ is trifluoromethylthio;
The malononitrile compounds of formula (Y) wherein $R^3$ is trifluoromethyl, m is 1, and $R^6$ is chlorine;
The malononitrile compounds of formula (Y) wherein $R^3$ is trifluoromethyl, m is 1, and $R^6$ is fluorine;
The malononitrile compounds of formula (Y) wherein $R^3$ is trifluoromethyl, m is 1, and $R^6$ is cyano;
The malononitrile compounds of formula (Y) wherein $R^3$ is trifluoromethyl, m is 1, and $R^6$ is nitro;
The malononitrile compounds of formula (Y) wherein $R^3$ is trifluoromethyl, m is 3, and $R^6$ is trifluoromethyl;
The malononitrile compounds of formula (Y) wherein $R^3$ is trifluoromethyl, m is 3, and $R^6$ is trifluoromethoxy;
The malononitrile compounds of formula (Y) wherein $R^3$ is trifluoromethyl, m is 3, and $R^6$ is trifluoromethylthio;
The malononitrile compounds of formula (Y) wherein $R^3$ is trifluoromethyl, m is 3, and $R^6$ is chlorine;
The malononitrile compounds of formula (Y) wherein $R^3$ is trifluoromethyl, m is 3, and $R^6$ is fluorine;
The malononitrile compounds of formula (Y) wherein $R^3$ is trifluoromethyl, m is 3, and $R^6$ is cyano;
The malononitrile compounds of formula (Y) wherein $R^3$ is trifluoromethyl, m is 3, and $R^6$ is nitro;
The malononitrile compounds of formula (Y) wherein $R^3$ is 2,2-dichlorovinyl, m is 1, and $R^6$ is trifluoromethyl;
The malononitrile compounds of formula (Y) wherein $R^3$ is 2,2-dichlorovinyl, m is 1, and $R^6$ is trifluoromethoxy;
The malononitrile compounds of formula (Y) wherein $R^3$ is 2,2-dichlorovinyl, m is 1, and $R^6$ is trifluoromethylthio;
The malononitrile compounds of formula (Y) wherein $R^3$ is 2,2-dichlorovinyl, m is 1, and $R^6$ is chlorine;
The malononitrile compounds of formula (Y) wherein $R^3$ is 2,2-dichlorovinyl, m is 1, and $R^6$ is fluorine;
The malononitrile compounds of formula (Y) wherein $R^3$ is 2,2-dichlorovinyl, m is 1, and $R^6$ is cyano;
The malononitrile compounds of formula (Y) wherein $R^3$ is 2,2-dichlorovinyl, m is 1, and $R^6$ is nitro;
The malononitrile compounds of formula (Y) wherein $R^3$ is 2,2-difluorovinyl, m is 1, and $R^6$ is trifluoromethyl;
The malononitrile compounds of formula (Y) wherein $R^3$ is 2,2-difluorovinyl, m is 1, and $R^6$ is trifluoromethoxy;
The malononitrile compounds of formula (Y) wherein $R^3$ is 2,2-difluorovinyl, m is 1, and $R^6$ is trifluoromethylthio;
The malononitrile compounds of formula (Y) wherein $R^3$ is 2,2-difluorovinyl, m is 1, and $R^6$ is chlorine;
The malononitrile compounds of formula (Y) wherein $R^3$ is 2,2-difluorovinyl, m is 1, and $R^6$ is fluorine;
The malononitrile compounds of formula (Y) wherein $R^3$ is 2,2-difluorovinyl, m is 1, and $R^6$ is cyano;
The malononitrile compounds of formula (Y) wherein $R^3$ is 2,2-difluorovinyl, m is 1, and $R^6$ is nitro;
The malononitrile compounds of formula (Y) wherein $R^3$ is 3,3,3-trifluoro-1-propenyl, m is 1, and $R^6$ is trifluoromethyl;
The malononitrile compounds of formula (Y) wherein $R^3$ is 3,3,3-trifluoro-1-propenyl, m is 1, and $R^6$ is trifluoromethoxy;
The malononitrile compounds of formula (Y) wherein $R^3$ is 3,3,3-trifluoro-1-propenyl, m is 1, and $R^6$ is trifluoromethylthio;
The malononitrile compounds of formula (Y) wherein $R^3$ is 3,3,3-trifluoro-1-propenyl, m is 1, and $R^6$ is chlorine;
The malononitrile compounds of formula (Y) wherein $R^3$ is 3,3,3-trifluoro-1-propenyl, m is 1, and $R^6$ is fluorine;
The malononitrile compounds of formula (Y) wherein $R^3$ is 3,3,3-trifluoro-1-propenyl, m is 1, and $R^6$ is cyano;
The malononitrile compounds of formula (Y) wherein $R^3$ is 3,3,3-trifluoro-1-propenyl, m is 1, and $R^6$ is nitro;
The malononitrile compounds of formula (Y) wherein $R^3$ is 3,3,3-trifluoro-1-propynyl, m is 1, and $R^6$ is trifluoromethyl;
The malononitrile compounds of formula (Y) wherein $R^3$ is 3,3,3-trifluoro-1-propynyl, m is 1, and $R^6$ is trifluoromethoxy;
The malononitrile compounds of formula (Y) wherein $R^3$ is 3,3,3-trifluoro-1-propynyl, m is 1, and $R^6$ is trifluoromethylthio;
The malononitrile compounds of formula (Y) wherein $R^3$ is 3,3,3-trifluoro-1-propynyl, m is 1, and $R^6$ is chlorine;
The malononitrile compounds of formula (Y) wherein $R^3$ is 3,3,3-trifluoro-1-propynyl, m is 1, and $R^6$ is fluorine;
The malononitrile compounds of formula (Y) wherein $R^3$ is 3,3,3-trifluoro-1-propynyl, m is 1, and $R^6$ is cyano;
The malononitrile compounds of formula (Y) wherein $R^3$ is 3,3,3-trifluoro-1-propynyl, m is 1, and $R^6$ is nitro;
The malononitrile compounds of formula (Y) wherein $R^3$ is heptafluoropropyl, m is 1, and $R^6$ is trifluoromethyl;
The malononitrile compounds of formula (Y) wherein $R^3$ is heptafluoropropyl, m is 1, and $R^6$ is trifluoromethoxy;
The malononitrile compounds of formula (Y) wherein $R^3$ is heptafluoropropyl, m is 1, and $R^6$ is trifluoromethylthio;
The malononitrile compounds of formula (Y) wherein $R^3$ is heptafluoropropyl, m is 1, and $R^6$ is chlorine;
The malononitrile compounds of formula (Y) wherein $R^3$ is heptafluoropropyl, m is 1, and $R^6$ is fluorine;
The malononitrile compounds of formula (Y) wherein $R^3$ is heptafluoropropyl, m is 1, and $R^6$ is cyano;
The malononitrile compounds of formula (Y) wherein $R^3$ is heptafluoropropyl, m is 1, and $R^6$ is nitro;
The malononitrile compounds of formula (Y) wherein $R^3$ is pentafluoroethyl, m is 1, and $R^6$ is trifluoromethyl;
The malononitrile compounds of formula (Y) wherein $R^3$ is pentafluoroethyl, m is 1, and $R^6$ is trifluoromethoxy;

The malononitrile compounds of formula (Y) wherein $R^3$ is pentafluoroethyl, m is 1, and $R^6$ is trifluoromethylthio;
The malononitrile compounds of formula (Y) wherein $R^3$ is pentafluoroethyl, m is 1, and $R^6$ is chlorine;
The malononitrile compounds of formula (Y) wherein $R^3$ is pentafluoroethyl, m is 1, and $R^6$ is fluorine;
The malononitrile compounds of formula (Y) wherein $R^3$ is pentafluoroethyl, m is 1, and $R^6$ is cyano;
The malononitrile compounds of formula (Y) wherein $R^3$ is pentafluoroethyl, m is 1, and $R^6$ is nitro;
The malononitrile compounds of formula (Y) wherein $R^3$ is fluoromethyl, m is 1, and $R^6$ is trifluoromethyl;
The malononitrile compounds of formula (Y) wherein $R^3$ is fluoromethyl, m is 1, and $R^6$ is trifluoromethoxy;
The malononitrile compounds of formula (Y) wherein $R^3$ is fluoromethyl, m is 1, and $R^6$ is trifluoromethylthio;
The malononitrile compounds of formula (Y) wherein $R^3$ is fluoromethyl, m is 1, and $R^6$ is chlorine;
The malononitrile compounds of formula (Y) wherein $R^3$ is fluoromethyl, m is 1, and $R^6$ is fluorine;
The malononitrile compounds of formula (Y) wherein $R^3$ is fluoromethyl, m is 1, and $R^6$ is cyano;
The malononitrile compounds of formula (Y) wherein $R^3$ is fluoromethyl, m is 1, and $R^6$ is nitro;
The malononitrile compounds of formula (Y) wherein $R^3$ is fluoromethyl, m is 2, and $R^6$ is trifluoromethyl;
The malononitrile compounds of formula (Y) wherein $R^3$ is fluoromethyl, m is 2, and $R^6$ is trifluoromethoxy;
The malononitrile compounds of formula (Y) wherein $R^3$ is fluoromethyl, m is 2, and $R^6$ is trifluoromethylthio;
The malononitrile compounds of formula (Y) wherein $R^3$ is fluoromethyl, m is 2, and $R^6$ is chlorine;
The malononitrile compounds of formula (Y) wherein $R^3$ is fluoromethyl, m is 2, and $R^6$ is fluorine;
The malononitrile compounds of formula (Y) wherein $R^3$ is fluoromethyl, m is 2, and $R^6$ is cyano;
The malononitrile compounds of formula (Y) wherein $R^3$ is fluoromethyl, m is 2, and $R^6$ is nitro;
The malononitrile compounds of formula (Y) wherein $R^3$ is chloromethyl, m is 1, and $R^6$ is trifluoromethyl;
The malononitrile compounds of formula (Y) wherein $R^3$ is chloromethyl, m is 1, and $R^6$ is trifluoromethoxy;
The malononitrile compounds of formula (Y) wherein $R^3$ is chloromethyl, m is 1, and $R^6$ is trifluoromethylthio;
The malononitrile compounds of formula (Y) wherein $R^3$ is chloromethyl, m is 1, and $R^6$ is chlorine;
The malononitrile compounds of formula (Y) wherein $R^3$ is chloromethyl, m is 1, and $R^6$ is fluorine;
The malononitrile compounds of formula (Y) wherein $R^3$ is chloromethyl, m is 1, and $R^6$ is cyano;
The malononitrile compounds of formula (Y) wherein $R^3$ is chloromethyl, m is 1, and $R^6$ is nitro;
The malononitrile compounds of formula (Y) wherein $R^3$ is 1,1-difluoroethyl, m is 2, and $R^6$ is trifluoromethyl;
The malononitrile compounds of formula (Y) wherein $R^3$ is 1,1-difluoroethyl, m is 2, and $R^6$ is trifluoromethoxy;
The malononitrile compounds of formula (Y) wherein $R^3$ is 1,1-difluoroethyl, m is 2, and $R^6$ is trifluoromethylthio;
The malononitrile compounds of formula (Y) wherein $R^3$ is 1,1-difluoroethyl, m is 2, and $R^6$ is chlorine;
The malononitrile compounds of formula (Y) wherein $R^3$ is 1,1-difluoroethyl, m is 2, and $R^6$ is fluorine;
The malononitrile compounds of formula (Y) wherein $R^3$ is 1,1-difluoroethyl, m is 2, and $R^6$ is cyano;
The malononitrile compounds of formula (Y) wherein $R^3$ is 1,1-difluoroethyl, m is 2, and $R^6$ is nitro;
The malononitrile compounds of formula (Y) wherein $R^3$ is 1-(trifluoromethyl)vinyl, m is 1, and $R^6$ is trifluoromethyl;
The malononitrile compounds of formula (Y) wherein $R^3$ is 1-(trifluoromethyl)vinyl, m is 1, and $R^6$ is trifluoromethoxy;
The malononitrile compounds of formula (Y) wherein $R^3$ is 1-(trifluoromethyl)vinyl, m is 1, and $R^6$ is trifluoromethylthio;
The malononitrile compounds of formula (Y) wherein $R^3$ is 1-(trifluoromethyl)vinyl, m is 1, and $R^6$ is chlorine;
The malononitrile compounds of formula (Y) wherein $R^3$ is 1-(trifluoromethyl)vinyl, m is 1, and $R^6$ is fluorine;
The malononitrile compounds of formula (Y) wherein $R^3$ is 1-(trifluoromethyl)vinyl, m is 1, and $R^6$ is cyano;
The malononitrile compounds of formula (Y) wherein $R^3$ is 1-(trifluoromethyl)vinyl, m is 1, and $R^6$ is nitro;
The malononitrile compounds of formula (Y) wherein $R^3$ is 1-(trifluoromethyl)vinyl, m is 2, and $R^6$ is trifluoromethyl;
The malononitrile compounds of formula (Y) wherein $R^3$ is 1-(trifluoromethyl)vinyl, m is 2, and $R^6$ is trifluoromethoxy;
The malononitrile compounds of formula (Y) wherein $R^3$ is 1-(trifluoromethyl)vinyl, m is 2, and $R^6$ is trifluoromethylthio;
The malononitrile compounds of formula (Y) wherein $R^3$ is 1-(trifluoromethyl)vinyl, m is 2, and $R^6$ is chlorine;
The malononitrile compounds of formula (Y) wherein $R^3$ is 1-(trifluoromethyl)vinyl, m is 2, and $R^6$ is fluorine;
The malononitrile compounds of formula (Y) wherein $R^3$ is 1-(trifluoromethyl)vinyl, m is 2, and $R^6$ is cyano;
The malononitrile compounds of formula (Y) wherein $R^3$ is 1-(trifluoromethyl)vinyl, m is 2, and $R^6$ is nitro.

The preferred compounds among the present compounds are the compounds wherein $R^6$ is halogen, cyano, nitro, $C_1$–$C_4$ haloalkyl, $C_1$–$C_4$ haloalkyloxy or $C_1$–$C_4$ haloalkylthio; the compounds wherein n is 1 to 3 and at least one of $R^5$ is halogen, cyano, nitro, $C_1$–$C_4$ haloalkyl, $C_1$–$C_4$ haloalkyloxy or $C_1$–$C_4$ (halo)alkylthio; or the compounds wherein $R^3$ is 1,2,2-trifluorovinyl, trifluoromethyl, pentafluoroethyl, 3,3,3-trifluoro-1-propenyl, heptafluoropropyl, 1,1-difluoroethyl or 1-(trifluoromethyl)vinyl. More preferred compounds are the compounds wherein $R^6$ is halogen, cyano, nitro, $C_1$–$C_4$ fluoroalkyl, $C_1$–$C_4$ fluoroalkyloxy or $C_1$–$C_4$ fluoroalkylthio; the compounds wherein n is 1 to 3 and at least one of $R^5$ is halogen, cyano, nitro, $C_1$–$C_4$ fluoroalkyl, $C_1$–$C_4$ fluoroalkyloxy or $C_1$–$C_4$ fluoroalkylthio; or the compounds wherein m is 2 and $R^3$ is trifluoromethyl.

The following will describe the production processes for the present compounds.

The present compounds can be produced by, for example, the following (Production Process 1) or (Production Process 2).

(Production Process 1)

This is a process by reacting compound (a) with compound (b) in the presence of a base.

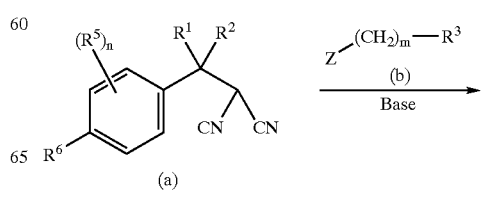

-continued

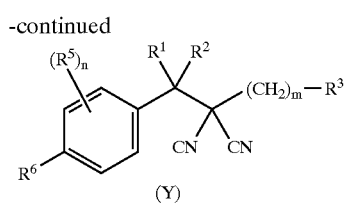

(Y)

wherein R¹, R², R³, R⁵, R⁶, m, and n are as defined above, and Z is halogen, methanesulfonyl, trifluoromethanesulfonyl, or toluenesulfonyl.

The reaction is usually carried out in a solvent. The solvent which can be used in the reaction may include acid amides such as dimethylformamide; ethers such as diethyl ether and tetrahydrofuran; organic sulfur compounds such as dimethylsulfoxide and sulfolane; halogenated hydrocarbons such as 1,2-dichloroethane and chlorobenzene; aromatic hydrocarbons such as toluene and xylene; water; and mixtures thereof The base which can be used in the reaction may include inorganic bases such as sodium hydride, sodium hydroxide, potassium hydroxide, and potassium carbonate; alkali metal alkoxides such as sodium methoxide, sodium ethoxide, and potassium tert-butoxide; alkali metal amides such as lithium diisopropylamide; and organic bases such as 4-dimethylaminopyridine, 1,4-diazabicyclo[2.2.2]octane, and 1,8-diazabicylco[5.4.0]-7-undecene. The amount of base used in the reaction is usually in a ratio of 1 to 10 moles relative to 1 mole of compound (a).

The reaction temperature is usually in the range of −20° C. to 100° C.

The reaction time is usually in the range of 1 to 24 hours.

The amount of compound (b) used in the reaction is usually in a ratio of 1 to 10 moles relative to 1 mole of compound (a).

After the reaction, the reaction mixture is poured into water, followed by ordinary post-treatment procedures including extraction with an organic solvent and concentration, thereby isolating the desired present compounds, which may be purified by a technique such as chromatography or recrystallization.

(Production Process 2)

This is a process by reacting compound (c) with compound (d) in the presence of a base.

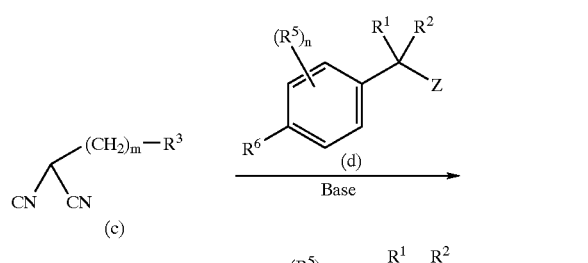

wherein R¹, R², R³, R⁵, R⁶, m, n, and Z are as defined above.

The reaction is usually carried out in a solvent. The solvent which can be used in the reaction may include acid amides such as dimethylformamide; ethers such as diethyl ether and tetrahydrofuran; organic sulfur compounds such as dimethylsulfoxide and sulfolane; halogenated hydrocarbons such as 1,2-dichloroethane and chlorobenzene; aromatic hydrocarbons such as toluene and xylene; water; and mixtures thereof The base which can be used in the reaction may include inorganic bases such as sodium hydride, sodium hydroxide, potassium hydroxide, and potassium carbonate; alkali metal alkoxides such as sodium methoxide, sodium ethoxide, and potassium tert-butoxide; alkali metal amides such as lithium diisopropylamide; and organic bases such as 4-dimethylaminopyridine, 1,4-diazabicyclo[2.2.2]octane, and 1,8-diazabicylco[5.4.0]-7-undecene. The amount of base used in the reaction is usually in a ratio of 1 to 10 moles relative to 1 mole of compound (a).

The reaction temperature is usually in the range of −20° C. to 100° C.

The reaction time is usually in the range of 1 to 24 hours.

The amount of compound (b) used in the reaction is usually in a ratio of 1 to 10 moles relative to 1 mole of compound (a).

After the reaction, the reaction mixture is poured into water, followed by ordinary post-treatment procedures including extraction with an organic solvent and concentration, thereby isolating the desired present compounds, which may be purified by a technique such as chromatography or recrystallization.

The compound (a) can be produced through a route, for example, as shown in the following scheme.

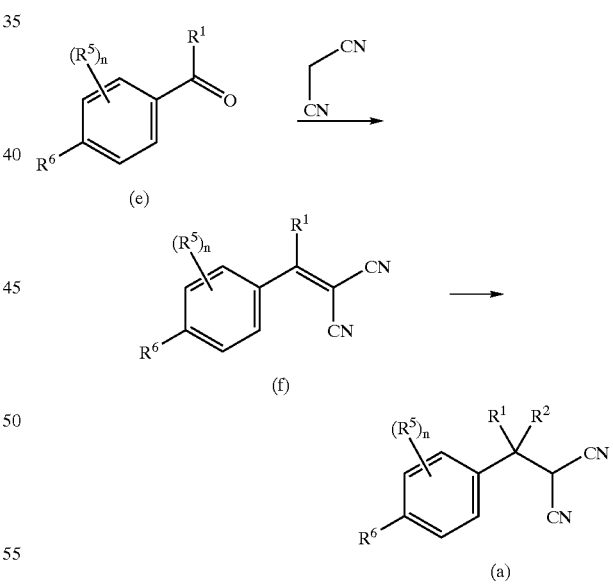

wherein R¹, R², R⁵, R⁶, and n are as defined above.

(Step 1)

The compound (f) can be produced by reacting compound (e) with malononitrile.

The reaction is usually carried out in a solvent and in the presence of a base. The solvent which can be used in the reaction may include acid amides such as N,N-dimethylformamide; ethers such as diethyl ether and tetrahydrofuran; halogenated hydrocarbons such as chloroform, 1,2-dichloroethane, and chlorobenzene; aromatic hydrocarbons such as toluene and xylene; alcohols such as methanol, ethanol, and isopropanol; and mixtures thereof The base which can be used in the reaction may include tetrabutylammonium hydroxide. The amount of base used in the reaction is usually in a ratio of 0.01 to 0.5 mole relative to 1 mole of compound (e).

The amount of malononitrile used in the reaction is usually in a ratio of 1 to 10 moles relative to 1 mole of compound (e).

The reaction temperature is usually in the range of $-20°$ C. to $200°$ C.

The reaction time is usually in the range of 1 to 24 hours.

The reaction may be carried out, while removing, if necessary, water which is generated by the reaction, from the reaction system.

After the reaction, the reaction mixture is poured into water, followed by ordinary post-treatment procedures including extraction with an organic solvent and concentration, thereby isolating the desired present compounds, which may be purified by a technique such as chromatography or recrystallization.

(Step 2)

(1) The case where $R^2$ is a substituent other than hydrogen and cyano:

The compound (a) can be produced by reacting compound (f) with an organometallic compound.

The reaction is usually carried out in a solvent and, if necessary, in the presence of a copper salt.

The solvent which can be used in the reaction may include ethers such as diethyl ether and tetrahydrofuran; aromatic hydrocarbons such as toluene and xylene; and mixtures thereof The organometallic compound which can be used in the reaction may include organic magnesium compounds such as methyl magnesium iodide, ethyl magnesium bromide, isopropyl magnesium bromide, vinyl magnesium bromide, ethynyl magnesium bromide, and dimethyl magnesium; organic lithium compounds such as methyl lithium; organic zinc compounds such as diethyl zinc; and organic copper compounds such as trifluoromethyl copper. The amount of organometallic compound used in the reaction is usually in a ratio of 1 to 10 moles relative to 1 mole of compound (f).

The copper salt which can be used in the reaction may include copper (I) iodide and copper (I) bromide. The amount of copper salt used in the reaction is usually not greater than 1 mole relative to 1 mole of compound (f).

The reaction temperature is usually in the range of $-20°$ C. to $100°$ C.

The reaction time is usually in the range of 1 to 24 hours.

After the reaction, the reaction mixture is poured into water, followed by ordinary post-treatment procedures including extraction with an organic solvent and concentration, thereby isolating the desired present compounds, which may be purified by a technique such as chromatography or recrystallization.

(2) The case where $R^2$ is hydrogen:

The compound (a) can be produced by subjecting compound (f) to reduction.

The reduction is usually carried out in a solvent.

The solvent which can be used in the reaction may include ethers such as diethyl ether and tetrahydrofuran; aromatic hydrocarbons such as toluene and xylene; alcohols such as methanol, ethanol, and propanol; water; and mixtures thereof.

The reducing agent which can be used in the reaction may include sodium borohydride. The amount of reducing agent used in the reaction is usually in a ratio of 0.25 to 2 moles relative to 1 mole of compound (f).

The reaction time is usually in the range of a moment to 24 hours.

The reaction temperature is usually in the range of $0°$ C. to $50°$ C.

After the reaction, the reaction mixture is poured into water, followed by ordinary post-treatment procedures including extraction with an organic solvent and concentration, thereby isolating the desired present compounds, which may be purified by a technique such as chromatography or recrystallization.

(3) The case where $R^2$ is cyano:

The compound (a) can be produced by reacting compound (f) with a cyanide.

The solvent which can be used in the reaction may include ethers such as diethyl ether and tetrahydrofuran; aromatic hydrocarbons such as toluene and xylene; and mixtures thereof.

The cyanide which can be used in the reaction may include tetrabutylammonium cyanide. The amount of cyanide used in the reaction is usually in a ratio of 1 to 10 moles relative to 1 mole of compound (f).

The reaction temperature is usually in the range of $-20°$ C. to $100°$ C.

The reaction time is usually in the range of 1 to 24 hours.

After the reaction, the reaction mixture is poured into water, followed by ordinary post-treatment procedures including extraction with an organic solvent and concentration, thereby isolating the desired present compounds, which may be purified by a technique such as chromatography or recrystallization.

The pests against which the present compounds exhibit controlling activity may include insect pests, acarine pests, and nematode pests, specific examples which are as follows:

Hemiptera:

Delphacidae such as *Laodelphax striatellus, Nilaparvata lugens,* and *Sogatella furcifera;*

Deltocephalidae such as *Nephotettix cincticeps* and *Nephotettix virescens;*

Aphididae such as *Aphis gossypii* and *Myzus persicae;*

Pentatomidae such as *Nezara antennata, Riptortus clavetus Eysarcoris lewisi, Eysarcoris parvus, Plautia stali* and *Halyomorpha misia;*

Aleyrodidae such as *Trialeurodes vaporariorum* and *Bemisia argentifolii;*

Coccidae such as *Aonidiella aurantii, Comstockaspis perniciosa, Unaspis citri, Ceroplastes rubens,* and *Icerya purchasi;*

Tingidae;

Psyllidae;

Lepidoptera:

Pyralidae such as *Chilo suppressalis, Cnaphalocrocis medinalis, Notarcha derogata,* and *Plodia interpunctella;*

Noctuidae such as *Spodoptera litura, Pseudaletia separata, Thoricoplusia* spp., *Heliothis* spp., and *Helicoverpa* spp.;

Pieridae such as *Pieris rapae;*

Tortricidae such as *Adoxophyes* spp., *Grapholita molesta,* and *Cydia pomonella;*

Carposinidae such as *Carposina niponensis;*

Lyonetiidae such as *Lyonetia* spp.;

Lymantriidae such as *Lyamantria* spp. and *Euproctis* spp.;

Yponomentidae such as *Plutella xylostella;*

Gelechiidae such as *Pectinophora gossypiella;*

Arctiidae such as *Hyphantria cunea;*

Tineidae such as *Tinea translucens* and *Tineola bisselliella*;

Diptera:

Calicidae such as *Culex pipiens pallens, Culex tritaeniorhynchus*, and *Culex quinquefasciatus*;

*Aedes* spp. such as *Aedes aegypti* and *Aedes albopictus*, *Anopheles* spp. such as *Anopheles sinensis*;

Chironomidae;

Muscidae such as *Musca domestica* and *Muscina stabulans*;

Calliphoridae;

Sarcophagidae;

Fanniidae;

Anthomyiidae such as *Delia platura* and *Delia antiqua*;

Tephritidae;

Drosophilidae;

Psychodidae;

Simuliidae;

Tabanidae;

Stomoxyidae;

Agromyzidae;

Coleoptera:

*Diabrotica* spp. such as *Diabrotica virgifera* and *Diabrotica undecimpunctata howardi*;

Scarabaeidae such as *Anomala cuprea* and *Anomala rufocuprea*;

Curculionidae such as *Sitophilus zeamais, Lissorhoptrus oryzophilus*, and *Callosohruchuys chienensis*;

Tenebrionidae such as *Tenebrio molitor* and *Tribolium castaneum*;

Chrysomelidae such as *Oulema oryzae, Aulacophora femoralis, Phyllotreta striolata*, and *Leptinotarsa decemlineata*;

Anobiidae;

*Epilachna* spp. such as *Epilachna vigintioctopunctata*;

Lyctidae;

Bostrychidae;

Cerambycidae;

*Paederus fuscipes*;

Dictyoptera:

*Blattella germanica, Periplaneta fuliginosa, Periplaneta americana, Periplaneta brunnea*, and *Blatta orientalis*;

Thysanoptera:

*Thrips palmi, Thrips tabaci, Frankliniella occidentalis, Frankliniella intonsa*;

Hymenoptera:

Formicidae;

Vespidae;

Bethylidae;

Tenthredinidae such as *Athalia japonica*;

Orthoptera:

Gryllotalpidae;

Acrididae;

Siphonaptera:

*Ctenocephalides felis, Ctenocephalides canis, Pulex irritans, Xenopsylla cheopis*;

Anoplura:

*Pediculus humanus corporis, Phthirus pubis, Haematopinus eurysternus*, and *Dalmalinia ovis*;

Isoptera:

*Reticulitermes speratus* and *Coptotermes formosanus*;

Acarina:

Tetranychidae such as *Tetranychus urticae, Tetranychus kanzawai, Panonychus citri, Panonychus ulmi*, and *Oligonychus* spp.;

Eriophyidae such as *Aculops pelekassi* and *Aculus schlechtendali*;

Tarsonemidae such as *Polyphagotarsonemus latus*;

Tenuipalpidae;

Tuckerellidae;

Ixodidae such as *Haemaphysalis longicornis, Haemaphysalis flava, Dermacentor taiwanicus, Ixodes ovatus, Ixodes persulcatus*, and *Boophilus microplus*;

Acaridae such as *Tyrophagus putrescentiae*;

Epidermoptidae such as *Dermatophagoides farinae* and *Dermatophagoides ptrenyssnus*;

Cheyletidae such as *Cheyletus eruditus, Cheyletus malaccensis*, and *Cheyletus moorei*;

Dermanyssidae;

Arachnida:

*Chiracanthium japonicum* and *Latrodectus hasseltii*;

Chilopoda:

*Thereuonema hilgendorfi* and *Scolopendra subspinipes*;

Diplopoda:

*Oxidus gracilis* and *Nedyopus tambanus*;

Isopoda:

*Armadillidium vulgare*;

Gastropoda:

*Limax marginatus* and *Limax flavus*;

Nematoda:

*Pratylenchus coffeae, Pratylenchus fallax, Heterodera glycines, Globodera rostochiensis, Meloidogyne hapla*, and *Meloidogyne incognita*.

When the present compounds are used as the active ingredients of pesticide compositions, they may be used as such without addition of any other ingredients. However, they are usually used in admixture with solid carriers, liquid carriers and/or gaseous carriers, and if necessary, by addition of adjuvants such as surfactants, followed by formulation into various forms such emulsifiable concentrates, oil formulations, flowables, dusts, wettable powders, granules, paste formulations, microcapsule formulations, foams, aerosol formulations, carbon dioxide gas formulations, tablets, or resin formulations. These formulations may be used by processing into poison baits, shampoo, mosquito coils, electric mosquito mats, smokes, fumigants, or sheets.

In these formulations, the present compounds are usually contained each in an amount of 0.1% to 95% by weight.

The solid carrier which can be used in the formulation may include the following materials in fine powder or granular form: clays (e.g., kaolin clay, diatomaceous earth, bentonite, Fubasami clay, acid clay); talc, ceramic, and other inorganic minerals (e.g., sericite, quartz, sulfur, activated carbon, calcium carbonate, hydrated silica); and chemical fertilizers (e.g., ammonium sulfate, ammonium phosphate, ammonium nitrate, ammonium chloride, urea).

The liquid carrier may include aromatic or aliphatic hydrocarbons (e.g., xylene, toluene, alkylnaphthalene, phenylxylylethane, kerosine, light oils, hexane, cyclohexane); halogenated hydrocarbons (e.g., chlorobenzene, dichloromethane, dichloroethane, trichloroethane); alcohols (e.g., methanol, ethanol, isopropyl alcohol, butanol, hexanol, ethylene glycol); ethers (e.g., diethyl ether, ethylene glycol dimethyl ether, diethylene glycol monomethyl ether, diethylene glycol monoethyl ether, propylene glycol monomethyl ether, tetrahydrofuran, dioxane); esters (e.g., ethyl acetate, butyl acetate); ketones (e.g., acetone, methyl ethyl ketone, methyl isobutyl ketone, cyclohexanone); nitriles (acetonitrile, isobutyronitrile); sulfoxides (e.g., dimethylsulfoxide); acid amides (e.g., N,N-dimethylformamide, N,N-dimethylacetamide); vegetable oils (e.g., soy bean oil and cotton seed oil); plant essential oils (e.g., orange oil, hyssop oil, lemon oil); and water.

The gaseous carrier may include butane gas, Freon gas, liquefied petroleum gas (LPG), dimethyl ether, and carbon dioxide.

The surfactant may include alkyl sulfate salts; alkylsulfonic acid salts; alkylarylsulfonic acid salts; alkyl aryl ethers and their polyoxyethylene derivatives; polyethylene glycol ethers; polyol esters; and sugar alcohol derivatives.

The other adjuvants may include binders, dispersants, and stabilizers, specific examples of which are casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (mixtures of 2-t-butyl-4-methoxyphenol and 3-t-butyl-4-methoxyphenol), vegetable oils, mineral oils, fatty acids, and fatty acid esters.

The base material for resin formulations may include vinyl chloride polymers and polyurethanes. These base materials may contain, if necessary, plasticizers such as phthalic acid esters (e.g., dimethyl phthalate, dioctyl phthalate), adipic acid esters, and stearic acid. The resin formulations can be obtained by kneading the present compounds into the base materials with an ordinary kneader and subsequent forming such as injection molding, extrusion, or pressing. They can be processed, if necessary, though further forming and cutting into resin formulations in various shapes such as plates, films, tapes, nets, or strings. These resin formulations are processed as, for example, collars for animals, ear tags for animals, sheet formulations, attractive strings, or poles for horticultural use.

The base material for poison baits may include grain powders, vegetable oils, sugars, and crystalline cellulose. If necessary, additional agents may be added, including antioxidants such as dibutylhydroxytoluene and nordihydroguaiaretic acid; preservatives such as dehydroacetic acid; agents for preventing children and pets from erroneously eating, such as hot pepper powder; and pest-attractive flavors such as cheese flavor, onion flavor, and peanut oil.

The pesticide compositions of the present invention may be used by, for example, direct application to pests and/or application to the habitats of pests (e.g., plant bodies, animal bodies, soil).

When the pesticide compositions of the present invention are used for the control of pests in agriculture and forestry, their application amounts are usually 1 to 10,000 g/ha, preferably 10 to 500 g/ha. Formulations such as emulsifiable concentrates, wettable powders, flowables, and microcapsule formulations are usually used after dilution with water to have an active ingredient concentration of 1 to 1000 ppm, while formulations such as dusts and granules are usually used as such. These formulations may be directly applied to plants to be protected from pests. These formulations can also be incorporated into soil for the control of pests inhabiting the soil, or can also be applied to beds before planting or applied to planting holes or plant bottoms in the planting. Further, the pesticide compositions of the present invention in the form of sheet formulations can be applied by the methods in which the sheet formulations are wound around plants, disposed in the vicinity of plants, or laid on the soil surface at the plant bottoms.

When the pesticide compositions of the present invention are used for the prevention of epidemics, their application amounts as active ingredient amounts are usually 0.001 to 10 mg/m$^3$ for spatial application or 0.001 to 100 mg/m$^2$ for planar application. Formulations such as emulsifiable concentrates, wettable powders, and flowables are usually applied after dilution with water to have an active ingredient concentration of 0.01 to 10,000 ppm, while formulations such as oil formulations, aerosols, smokes, or poison baits are usually applied as such.

When the pesticide compositions of the present invention are used for the control of external parasites on domestic animals such as cattle, sheep, goat, and fowl or small animals such as dogs, cats, rats, and mice, they can be used by the veterinarily well-known methods. As the specific methods of use, administration is achieved by, for example, tablets, feed incorporation, suppositories, or injections (e.g., intramuscular, subcutaneous, intravenous, intraperitoneal) for systemic control, or by, for example, spraying, pour-on treatment, or spot-on treatment with an oil formulation or an aqueous solution, washing animals with a shampoo formulation, or attachment of a collar or ear tag prepared from a resin formulation to animals for non-systemic control. The amounts of the present compounds when administered to animal bodies are usually in the range of 0.1 to 1000 mg per 1 kg weight of each animal.

The pesticide compositions of the present invention can also be used in admixture or combination with other insecticides, nematocides, acaricides, bactericides, fungicides, herbicides, plant growth regulators, synergists, fertilizers, soil conditioners, animal feeds, and the like.

Examples of the insecticides and acaricides include organophosphorus compounds such as fenitrothion[O,O-dimethyl O-(3-methyl-4-nitrophenyl)phosphorothioate], fenthion[O,O-dimethyl O-(3-methyl-4-(methylthio)phenyl) phosphorothioate], diazinon[O,O-diethyl O-2-isopropyl-6-methylpyrimidin-4-yl phosphorothioate], chlorpyrifos[O,O-diethyl O-3,5,6-trichloro-2-pyridyl phosphorothioate], DDVP[2,2-dichlorovinyl dimethyl phosphate], cyanophos [O-4-cyanophenyl O,O-dimethyl phosphorothioate], dimethoate[O,O-dimethyl S-(N-methylcarbamoylmethyl) dithiophosphate], phenthoate[ethyl 2-dimethoxyphosphinothioylthio(phenyl)acetate], malathion[diethyl(dimethoxyphosphinothioylthio)succinate], and azinphosmethyl[S-3,4-dihydro-4-oxo-1,2,3-benzotriazin-3-ylmethyl O,O-dimethyl phosphorodithioate]; carbamate compounds such as BPMC (2-sec-butylphenyl methylcarbamate), benfracarb[ethyl N-[2,3-dihydro-2,2-dimethylbenzofuran-7-yloxycarbonyl (methyl)aminothio]-N-isopropyl-β-alaninate], propoxur[2-isopropoxyphenyl N-methylcarbamate] and carbaryl[1-naphthyl N-methylcarbamate]; pyrethroid compounds such as etofenprox[2-(4-ethoxyphenyl)-2-methylpropyl 3-phenoxybenzyl ether], fenvalerate[(RS)-α-cyano-3-phenoxybenzyl(RS)-2-(4-chlorophenyl)-3-methyl-butyrate], esfenvalerate[(S)-α-cyano-3-phenoxybenzyl(S)-2-(4-chlorophenyl)-3-methyl-butyrate], fenpropathrin[(RS)-α-cyano-3-phenoxybenzyl 2,2,3,3-tetramethylcyclopropanecarboxylate], cypermethrin[(RS)-α-cyano-3-phenoxybenzyl(1RS)-cis,trans-3-(2,2-dichlorovinyl)-2,2-dimethylcyclopropanecarboxylate], permethrin[3-phenoxybenzyl(1RS)-cis, trans-3-(2,2-dichlorovinyl)-2,2-dimethylcyclopropanecarboxylate], cyhalothrin[(RS)-α-cyano-3-phenoxybenzyl(Z)-(1RS)-cis-3-(2-chloro-3,3,3-trifluoroprop-1-enyl)-2,2-dimethylcyclopropanecarboxylate], deltamethrin[(S)-α-cyano-3-phenoxybenzyl(1R)-cis-3-(2,2-dibromovinyl)-2,2-dimethylcyclopropane-carboxylate], cycloprothrin[(RS)-α-cyano-3-phenoxybenzyl(RS)-2,2-dichloro-1-(4-ethoxyphenyl)cyclopropanecarboxylate], fluvalinate[α-cyano-3-phenoxybenzyl N-(2-chloro-α,α,α-trifluoro-p-tolyl)-D-valinate], bifenthrin[2-methylbiphenyl-3-ylmethyl (Z)-(1RS)-cis-3-(2-chloro-3,3,3-trifluoroprop-1-enyl)-2,2-dimethylcyclopropanecarboxylate], 2-methyl-2-(4- bromodifluoro-methoxyphenyl)propyl 3-phenoxybenzyl ether, tralomethrin[(S)-α-cyano-3-phenoxybenzyl(1R)-cis)-3-{(1RS)( 1,2,2,2-tetrabromoethyl)}-2,2-dimethyl-cyclopropanecarboxylate], silafluofen[(4-ethoxyphenyl){3-(4-fluoro-3-phenoxyphenyl)propyl}-dimethylsilane], d-phenothrin-[3-phenoxybenzyl(1R)-cis,trans)-chrysanthemate], cyphenothrin[(RS)-α-cyano-3-phenoxybenzyl(1R)-cis,trans)-chrysanthemate], d-resmethrin[5-benzyl-3-furylmethyl(1R)-cis,trans)-chrysanthemate], acrinathrin[(S)-α-cyano-3-phenoxybenzyl(1R,cis(Z))-2,2-dimethyl- 3-{3-oxo-3-(1,1,1,3,3,3-hexafluoropropyloxy) propenyl}cyclopropanecarboxylate], cyfluthrin[(RS)-α-cyano-4-fluoro-3-phenoxybenzyl 3-(2,2-dichlorovinyl)-2,2-dimethylcydopropanecarboxylate], tefluthrin[2,3,5,6-tetrafluoro-4-methylbenzyl(1RS-cis(Z))-3-(2-chloro-3,3,3-trifluoroprop-1-enyl)-2,2-dimethylcyclopropanecarboxylate], transfluthrin[2,3,5,6-tetrafluorobenzyl(1R)-trans)-3-(2,2-dichlorovinyl)-2,2-dimethylcyclopropanecarboxylate], tetramethrin[3,4,5,6-tetrahydrophthalimidomethyl(1RS)-cis,trans-chrysanthemate], allethrin[(RS)-3-allyl-2-methyl-4-oxocyclopent-2-enyl(1RS)-cis,trans-chrysanthemate], prallethrin[(S)-2-methyl-4-oxo-3-(2-propynyl) cyclopent-2-enyl(1R)-cis,trans-chrysanthemate], empenthrin[(RS)-1-ethynyl-2-methyl-2-pentenyl(1R)-cis,trans-chrysanthemate], imiprothrin[2,5-dioxo-3-(prop-2-ynyl)imidazolidin-1-ylmethyl(1R)-cis,trans-2,2-dimethyl-3-(2-methylprop-1-enyl)cyclopropanecarboxylate], d-furamethrin[5-(2-propynyl)furfuryl(1R)-cis,trans-chrysanthemate] and 5-(2-propynyl)furfuryl 2,2,3,3-tetramethylcyclopropanecarboxylate; neonicotinoid derivatives such as N-cyano-N'-methyl-N'-(6-chloro-3-pyridylmethyl)acetamidine; nitenpyram[N-(6-chloro-3-pyridylmethyl)-N-ethyl-N'-methyl-2-nitrovynylidenediamine]; thiacloprid[1-(2-chloro-5-pyridylmethyl)-2-cyanoiminothiazoline]; thiamethoxam[3-((2-chloro-5-thiazolyl)methyl)-5-methyl-4-nitroiminotetrahydro-1,3,5-oxadiazine], 1-methyl-2-nitro-3-((3-tetrahydrofuryl)methyl) guanidine and 1-(2-chloro-5-thiazolyl)methyl-3-methyl-2-nitroguanidine; nitroiminohexahydro-1,3,5-triazine derivatives; chlorinated hydrocarbons such as endosulfan[6,7,8,9,10,10-hexachloro-1,5,5a,6,9,9α-hexahydro-6,9-methano-2,4,3-benzodioxathiepine oxide], γ-BHC[1,2,3,4,5,6-hexachlorocyclohexane] and 1,1-bis(chlorophenyl)-2,2,2-trichloroethanol; benzoylphenylurea compounds such as chlorfluazuron[1-(3,5-dichloro-4-(3-chloro-5-trifluoromethylpyridyn-2-yloxy)phenyl)-3-(2,6-difluorobenzoyl)urea], teflubenzuron[1-(3,5-dichloro-2,4-difluorophenyl)-3-(2,6-difluorobenzoyl)urea] and flufenoxuron[1-(4-(2-chloro-4-trifluoromethylphenoxy)-2-fluorophenyl)-3-(2,6-difluorobenzoyl)urea]; juvenile hormone like compounds such as pyriproxyfen[4-phenoxyphenyl 2-(2-pyridyloxy)propyl ether], methoprene[isopropyl (2E,4E)-11-methoxy-3,7,11-trimethyl-2,4-dodecadienoate] and hydroprene[ethyl(2E,4E)-11-methoxy-3,7,11-trimethyl-2,4-dodecadienoate]; thiourea derivatives such as diafenthiuron[N-(2,6-diisopropyl-4-phenoxyphenyl)-N'-tert-butylcarbodiimide]; phenylpyrazole compounds; 4-bromo-2-(4-chlorophenyl)-1-ethoxymethyl-5-trifluoromethylpyrrol-3-carbonitrile [chlorfenapil]; metoxadiazone[5-methoxy-3-(2-methoxyphenyl)-1,3,4-oxadiazol-2(3H)-one], bromopropylate[isopropyl 4,4'-dibromobenzilate], tetradifon[4-chlorophenyl 2,4,5-trichlorophenyl sulfone], chinomethionat[S,S-6-methylquinoxaline-2,3-diyldithiocarbonate], pyridaben[2-tert-butyl-5-(4-tertbutylbenzylthio)-4-chloropyridazin-3(2H)-one], fenpyroximate[tert-butyl(E)-4-[(1,3-dimethyl-5-phenoxypyrazol-4-yl) methyleneaminooxymethyl]benzoate], tebufenpyrad[N-(4-tert-butylbenzyl)-4-chloro-3-ethyl-1-methyl-5-pyrazolecarboxamide], polynactins complex [tetranactin, dinactin and trinactin], pyrimidifen[5-chloro-N-[2-{4-(2-ethoxyethyl)-2,3-dimethylphenoxy}ethyl]-6-ethylpyrimidin-4-amine], milbemectin, abamectin, ivermectin and azadirachtin[AZAD]. Examples of the synergists include bis-(2,3,3,3-tetrachloropropyl)ether(S-421), N-(2-ethylhexyl) bicyclo[2.2.1]hept-5-ene-2,3-dicarboximide (MGK-264) and α-[2-(2-butoxyethoxy)ethoxy]-4,5-methylenedioxy-2-propyltoluene (piperonyl butoxide).

The present invention will further be illustrated by the following production examples, formulation examples, and test examples; however, the present invention is not limited only to these examples. In the formulation examples, the present compound numbers are those shown in Table 1 below.

The following will describe some production examples for the present compounds.

PRODUCTION EXAMPLE 1

First, 0.50 g of (4-chlorobenzyl)malononitrile was dissolved in 10 ml of N,N-dimethylformamide, to which 0.16 g of sodium hydride (60% in oil) was added under ice cooling. After the evolution of hydrogen gas ceased, while stirring under ice cooling, 0.48 ml of 2,3-dichloropropene was added dropwise, followed by stirring at room temperature for 5 hours. Then, 10% hydrochloric acid was added to the reaction mixture, which was extracted with diethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 0.19 g of 2-(4-chlorobenzyl)-2-(2-chloro-2-propenyl)malononitrile (the present compound (1)).

Yield: 27%;

m.p.: 85.5° C.

PRODUCTION EXAMPLE 2

Using 0.50 g of (4-(trifluoromethylthio)benzyl)malononitrile, 5 ml of N,N-dimethylformamide, 90 mg of sodium hydride (60% in oil), and 0.26 g of 2,3-dichloropropene, and according to the process described in the Production Example 1, there was obtained 0.30 g of 2-(2-chloro-2-propenyl)-2-(4-(trifluoromethylthio)benzyl)malononitrile (the present compound (2)).

Yield: 47%;

$^1$H-NMR (CDCl$_3$, TMS, δ (ppm)): 3.05 (2H, s), 3.32 (2H, s), 5.58–5.66 (2H, m), 7.48 (2H, d), 7.73 (2H, d).

PRODUCTION EXAMPLE 3

Using 0.1 g of benzylmalononitrile, 5 ml of N,N-dimethylformamide, 0.073 g of cesium carbonate, and 0.1 g of 2,2,2-trifluoroethyl trifluoromethanesulfonate, and according to the process described in the Production Example 1, there was obtained 0.057 g of 2-benzyl-2-(2,2,2-trifluoroethyl)malononitrile (the present compound (3)).

Yield: 40%;

$^1$H-NMR (CDCl$_3$, TMS, δ (ppm)): 2.76 (2H, q), 3.36 (2H, s), 7.37–7.47 (5H, m).

PRODUCTION EXAMPLE 4

Using 0.1 g of benzylmalononitrile, 5 ml of N,N-dimethylformamide, 0.010 g of sodium hydride (60% in oil), and 0.04 g of 4-bromo-1,1,2-trifluoro-1-butene, and according to the process described in the Production Example 1, there was obtained 0.042 g of 2-benzyl-2-(3,4,4-trifluoro-3-butenyl)malononitrile (the present compound (4)).

Yield: 57%;
$^1$H-NMR (CDCl$_3$, TMS, δ (ppm)): 2.17–2.23 (2H, m), 2.64–2.78 (2H, m), 3.27 (2H, s), 7.34–7.45 (5H, m).

PRODUCTION EXAMPLE 5

Using 0.3 g of (4-(trifluoromethoxy)benzyl)malononitrile, 5 ml of N,N-dimethylformamide, 0.073 g of cesium carbonate, and 0.35 g of 2,2,3,3,3-pentafluoropropyl trifluoromethanesulfonate, and according to the process described in the Production Example 1, there was obtained 0.12 g of 2-(2,2,3,3,3-pentafluoropropyl)-2-(4-(trifluoromethoxy)benzyl)malononitrile (the present compound (5)).

Yield: 29%;
$^1$H-NMR (CDCl$_3$, TMS, δ (ppm)): 2.76 (2H, t), 3.38 (2H, s), 7.30 (2H, d), 7.46 (2H, d)

PRODUCTION EXAMPLE 6

Using 0.3 g of (3,3,3-trifluoropropyl)malononitrile, 3 ml of N,N-dimethylformamide, 0.08 g of sodium hydride (60% in oil), and 0.4 g of 4-acetylbenzyl bromide, and according to the process described in the Production Example 1, there was obtained 0.43 g of 2-(4-acetylbenzyl)-2-(3,3,3-trifluoropropyl)malononitrile (the present compound (6)).

Yield: 78%;
$^1$H-NMR (CDCl$_3$, TMS, δ (ppm)): 2.22–2.34 (2H, m), 2.51–2.61 (2H, m), 2.67 (3H, s), 3.42 (2H, s), 7.50 (2H, d), 7.97 (2H, d).

PRODUCTION EXAMPLE 7

Using 0.30 g of (2,6-dichloro-4-(trifluoromethyl)benzyl)malononitrile, 5 ml of N,N-dimethylformamide, 0.05 g of sodium hydride (60% in oil), and 0.20 g of 1-bromo-3,3,3-trifluoropropane, and according to the process described in the Production Example 1, there was obtained 0.21 g of 2-(2,6-dichloro-4-(trifluoromethyl)benzyl)-2-(3,3,3-trifluoropropyl)malononitrile (the present compound (7)).

Yield: 53%;
$^1$H-NMR (CDCl$_3$, TMS, δ (ppm)): 2.41–2.49 (2H, m), 2.52–2.63 (2H, m), 3.79 (2H, s), 7.68 (2H, s).

PRODUCTION EXAMPLE 8

Using 0.30 g of (4-(trifluoromethyl)benzyl)malononitrile, 6 ml of N,N-dimethylformamide, 0.60 g of sodium hydride (60% in oil), and 0.38 g of 4-iodo-1,1,1,2,2-pentafluorobutane, and according to the process described in the Production Example 1, there was obtained 0.30 g of 2-(3,3,4,4,4-pentafluorobutyl)-2-(4-(trifluoromethyl)benzyl)malononitrile (the present compound (8)).

Yield: 54%;
$^1$H-NMR (CDCl$_3$, TMS, Δ (ppm)): 2.27–2.62 (4H, m), 3.86 (2H, s), 7.53 (2H, d), 7.71 (2H, d).

And there was obtained 15 mg of 2-(3,4,4,4-tetrafluoro-2-butenyl)-2-(4-(trifluoromethyl)benzyl)malononitrile (the present compound (48)) as low-polar compound.

Yield: 3%;
$^1$H-NMR (CDCl$_3$, TMS, δ (ppm)): 2.96 (2H, d), 3.30 (2H, s), 5.78 (1H, dt), 7.53 (2H, d), 7.71 (2H, d).

PRODUCTION EXAMPLE 9

Using 3.86 g of (4-bromobenzyl)malononitrile, 25 ml of N,N-dimethylformamide, 0.72 g of sodium hydride (60% in oil), and 3.20 g of 1-bromo-3,3,3-trifluoropropane, and according to the process described in the Production Example 1, there was obtained 4.61 g of 2-(4-bromobenzyl)-2-(3,3,3-trifluoropropyl)malononitrile (the present compound (9)).

Yield: 85%;
$^1$H-NMR (CDCl$_3$, TMS, δ (ppm)): 2.18–2.27 (2H, m), 2.45–2.60 (2H, m), 3.22 (2H, s), 7.26 (2H, d), 7.57 (2H, d).

PRODUCTION EXAMPLE 10

Using 0.30 g of (4-(trifluoromethoxy)benzyl)malononitrile, 10 ml of N,N-dimethylformamide, 0.06 g of sodium hydride (60% in oil), and 0.38 g of 4-iodo-1,1,1,2,2-pentafluorobutane, and according to the process described in the Production Example 1, there was obtained 0.15 g of 2-(3,3,4,4,4-pentafluorobutyl)-2-(4-(trifluoromethoxy)benzyl)malononitrile (the present compound (10)).

Yield: 28%;
$^1$H-NMR (CDCl$_3$, TMS, δ (ppm)): 2.21–2.62 (4H, m), 3.30 (2H, s), 7.27 (2H, d), 7.43 (2H, d).

PRODUCTION EXAMPLE 11

Under nitrogen atmosphere, 0.40 g of 2-(2-formylethyl)-2-(4-(trifluoromethyl)benzyl)malononitrile was dissolved in 10 ml of trichlorofluoromethane, to which 0.20 ml of diethylaminosulfur trifluoride was added dropwise slowly, and then stirred for 30 minutes. Then, water was added to the reaction mixture, which was extracted with ethyl acetate. The organic layer was washed with a saturated aqueous sodium chloride solution, dried over anhydrous magnesium sulfate, and then concentrated under reduced pressure. The residue was subjected to silica gel column chromatography to give 0.15 g of 2-(3,3-difluoropropyl)-2-(4-(trifluoromethyl)benzyl)malononitrile (the present compound (11)).

Yield: 34%;
$^1$H-NMR (CDCl$_3$, TMS, δ (ppm)): 2.19–2.34 (4H, m), 3.31 (2H, s), 6.00 (1H, tt), 7.53 (2H, d), 7.71 (2H,d).

PRODUCTION EXAMPLE 12

Using 0.50 g of benzylmalononitrile, 10 ml of N,N-dimethylformamide, 0.14 g of sodium hydride (60% in oil), and 0.63 g of 1-bromo-3,3,3-trifluoropropane, and according to the process described in the Production Example 1, there was obtained 0.14 g of 2-benzyl-2-(3,3,3-trifluoropropyl)malononitrile (the present compound (12)).

Yield: 17%;
$^1$H-NMR (CDCl$_3$, TMS, δ (ppm)): 2.20–2.27 (2H, m), 2.45–2.59 (2H, m), 3.28 (2H, s), 7.34–7.48 (5H, m).

PRODUCTION EXAMPLE 13

Using 0.50 g of (4-(trifluoromethylthio)benzyl)malononitrile, 10 ml of N,N-dimethylformamide, 0.09 g of sodium hydride (60% in oil), and 0.38 g of 1-bromo-3,3,3-trifluoropropane, and according to the process described in the Production Example 1, there was obtained 0.03 g of 2-(4-

(trifluoromethylthio)benzyl)-2-(3,3,3-trifluoropropyl)malononitrile (the present compound (13)).
Yield: 11%;
$^1$H-NMR (CDCl$_3$, TMS, δ (ppm)): 2.20–2.29 (2H, m), 2.51–2.62 (2H, m), 3.29 (2H, s), 7.45 (2H, d), 7.73 (2H, d).

PRODUCTION EXAMPLE 14

Using 0.80 g of 2-(3-hydroxypropyl)-2-(4-(trifluoromethyl)benzyl)-malononitrile, 8 ml of dichloromethane and 0.3 ml of Diethylaminosulfur trifluoride, and according to the process described in the Production Example 11, there was obtained 0.05 g of 2-(3-fluoropropyl)-2-(4-(trifluoromethyl)benzyl)malononitrile (the present compound (14)).
Yield: 5%;
$^1$H-NMR (CDCl$_3$, TMS, δ (ppm)): 2.14–2.20 (4H, m), 3.30 (2H, s), 4.59 (2H, dt), 7.53 (2H, d), 7.69 (2H, d).

PRODUCTION EXAMPLE 15

Using 1.00 g of (4-chlorobenzyl)malononitrile, 10 ml of N,N-di-methylformamide, 1.0 g of sodium hydride (60% in oil), and 0.93 g of 1-bromo-3,3,3-trifluoropropane, and according to the process described in the Production Example 1, there was obtained 0.21 g of 2-(4-chlorobenzyl)-2-(3,3,3-trifluoropropyl)malononitrile (the present compound (15)).
Yield: 22%;
$^1$H-NMR (CDCl$_3$, TMS, δ (ppm)): 2.17–2.26 (2H, m), 2.48–2.63 (2H, m), 3.24 (2H, s), 7.32 (2H, d), 7.42 (2H, d).

PRODUCTION EXAMPLE 16

Using 1.00 g of (4-fluorobenzyl)malononitrile, 15 ml of N,N-di-methylformamide, 0.23 g of sodium hydride (60% in oil), and 1.02 g of 1-bromo-3,3,3-trifluoropropane, and according to the process described in the Production Example 1, there was obtained 0.34 g of 2-(4-fluorobenzyl)-2-(3,3,3-trifluoropropyl)malononitrile (the present compound (16)).
Yield: 22%;
$^1$H-NMR (CDCl$_3$, TMS, δ (ppm)): 2.20–2.27 (2H, m), 2.47–2.62 (2H, m), 3.24 (2H, s), 7.13 (2H, dd), 7.37 (2H, dd).

PRODUCTION EXAMPLE 17

Using 0.50 g of (2,4,6-trifluorobenzyl)malononitrile, 10 ml of N,N-di-methylformamide, 0.11 g of sodium hydride (60% in oil), and 0.46 g of 1-bromo-3,3,3-trifluoropropane, and according to the process described in the Production Example 1, there was obtained 0.07 g of 2-(2,4,6-trifluorobenzyl)-2-(3,3,3-trifluoropropyl)malononitrile (the present compound (17)).
Yield: 10%;
$^1$H-NMR (CDCl$_3$, TMS, δ (ppm)): 2.22–2.29 (2H, m), 2.50–2.61 (2H, m), 3.68 (2H, s), 6.82 (2H, dd).

PRODUCTION EXAMPLE 18

Using 5.00 g of (4-nitrobenzyl)malononitrile, 60 ml of N,N-di-methylformamide, 1.10 g of sodium hydride (60% in oil), and 4.85 g of 1-bromo-3,3,3-trifluoropropane, and according to the process described in the Production Example 1, there was obtained 0.80 g of 2-(4-nitrobenzyl)-2-(3,3,3-trifluoropropyl)malononitrile (the present compound (18)).
Yield: 11%;
$^1$H-NMR (CDCl$_3$, TMS, δ (ppm)): 2.28–2.32 (2H, m), 2.52–2.64 (2H, m), 3.40 (2H, s), 7.58 (2H, d), 8.33 (2H, d).

PRODUCTION EXAMPLE 19

Using 1.00 g of (3,4-difluorobenzyl)malononitrile, 10 ml of N,N-di-methylformamide, 0.20 g of sodium hydride (60% in oil), and 1.38 g of 1-bromo-3,3,3-trifluoropropane, and according to the process described in the Production Example 1, there was obtained 0.32 g of 2-(3,4-difluorobenzyl)-2-(3,3,3-trifluoropropyl)malononitrile (the present compound (19)).
Yield: 21%;
$^1$H-NMR (CDCl$_3$, TMS, δ (ppm)): 2.20–2.29 (2H, m), 2.50–2.61 (2H, m), 3.22 (2H, s), 7.11–7.15 (2H, m), 7.21–7.31 (2H, m).

PRODUCTION EXAMPLE 20

Using 0.50 g of (4-chlorobenzyl)malononitrile, 5 ml of N,N-di-methylformamide, 0.12 g of sodium hydride (60% in oil), and 0.30 ml of 1,1,3-trichloropropene, and according to the process described in the Production Example 1, there was obtained 0.52 g of 2-(4-chlorobenzyl)-2-(3,3-dichloro-2-propenyl)malononitrile (the present compound (20)).
Yield: 66%;
m.p.: 67.5° C.

PRODUCTION EXAMPLE 21

Using 2.00 g of (3,4-dichlorobenzyl)malononitrile, 20 ml of N,N-di-methylformamide, 0.36 g of sodium hydride (60% in oil), and 2.37 g of 1-bromo-3,3,3-trifluoropropane, and according to the process described in the Production Example 1, there was obtained 0.42 g of 2-(3,4-dichlorobenzyl)-2-(3,3,3-trifluoropropyl)malononitrile (the present compound (21)).
Yield: 45%;
$^1$H-NMR (CDCl$_3$, TMS, δ (ppm)): 2.22–2.29 (2H, m), 2.50–2.62 (2H, m), 3.21 (2H, s), 7.25 (1H, d), 7.51 (2H, dd).

PRODUCTION EXAMPLE 22

Using 1.00 g of (4-cyanobenzyl)malononitrile, 10 ml of N,N-di-methylformamide, 0.36 g of sodium hydride (60% in oil), and 2.37 g of 1-bromo-3,3,3-trifluoropropane, and according to the process described in the Production Example 1, there was obtained 0.42 g of 2-(4-cyanobenzyl)-2-(3,3,3-trifluoropropyl)malononitrile (the present compound (22)).
Yield: 22%;
$^1$H-NMR (CDCl$_3$, TMS, δ (ppm)): 2.25–2.30 (2H, m), 2.51–2.62 (2H, m), 3.31 (2H, s), 7.53 (2H, d), 7.76 (2H, d).

PRODUCTION EXAMPLE 23

Using 1.00 g of (4-chlorobenzyl)malononitrile, 10 ml of N,N-di-methylformamide, 0.21 g of sodium hydride (60% in oil), and 1.44 g of 4-iodo-1,1,1,2,2-pentafluorobutane, and according to the process described in the Production Example 1, there was obtained 0.47 g of 2-(4-chlorobenzyl)-2-(3,3,4,4,4-pentafluorobutyl)malononitrile (the present compound (23)).
Yield: 28%;
$^1$H-NMR (CDCl$_3$, TMS, δ (ppm)): 2.25–2.32 (2H, m), 2.41–2.53 (2H, m), 3.25 (2H, s), 7.33 (2H, d), 7.43 (2H, d).

PRODUCTION EXAMPLE 24

Using 1.00 g of (4-chlorobenzyl)malononitrile, 10 ml of N,N-di-methylformamide, 0.21 g of sodium hydride (60% in oil), and 0.67 g of 1-bromo-2-fluoroethane, and according to the process described in the Production Example 1, there was obtained 0.30 g of 2-(4-chlorobenzyl)-2-(2-fluoroethyl)malononitrile (the present compound (24)).

Yield: 22%;
$^1$H-NMR (CDCl$_3$, TMS, δ (ppm)): 2.39(2H, dt), 3.27 (2H, s), 4.83 (2H, dt), 7.34 (2H, d), 7.41 (2H, d).

PRODUCTION EXAMPLE 25

Using 1.0 g of (4-chlorobenzyl)malononitrile, 15 ml of N,N-di-methylformamide, 0.073 g of cesium carbonate, and 1.47 g of 2,2,3,3-tetra-fluoropropyl trifluoromethanesulfonate, and according to the process described in the Production Example 1, there was obtained 0.12 g of 2-(4-chlorobenzyl)-2-(2,2,3,3-tetrafluoropropyl)malononitrile (the present compound (25)).

Yield: 7%;
$^1$H-NMR (CDCl$_3$, TMS, δ (ppm)): 2.69 (2H, t), 3.31 (2H, s), 5.87 (1H, tt), 7.34 (2H, d), 7.41 (2H, d).

PRODUCTION EXAMPLE 26

First, 0.55 g of 4-iodobenzyl bromide was dissolved in 10 ml of N,N-dimethylformamide, to which the suspension of 0.11 g of sodium hydride (60% in oil) and 0.30 g of (3,3,3-trifluoropropyl)malononitrile in 5 ml of N,N-dimethylformamide was added dropwise, while stirring under ice cooling. After stirring for 4 hours at 0° C., 10% hydrochloric acid was added to the reaction mixture at room temperature, which was extracted with ethyl acetate. The organic layer was successively washed with water, a saturated aqueous sodium chloride solution, dried over anhydrous magnesium sulfate, and then concentrated under reduced pressure. The residue was subjected to silica gel column chromatography to give 0.16 g of 2-(4-iodobenzyl)-2-(3,3,3-trifluoropropyl)malononitrile (the present compound (26)).

Yield: 22%;
$^1$H-NMR (CDCl$_3$, TMS, δ (ppm)): 2.17–2.23 (2H, m), 2.49–2.60 (2H, m), 3.22 (2H, s), 7.11 (2H, d), 7.78 (2H, d).

PRODUCTION EXAMPLE 27

Using 0.15 g of (4-vinylbenzyl)chloride, 3 ml of N,N-dimethylformamide, 0.05 g of sodium hydride (60% in oil) and 0.17 g of (3,3,3-trifluoropropyl)malononitrile, and according to the process described in the Production Example 27, there was obtained 0.18 g of 2-(3,3,3-trifluoropropyl)-2-(4-vinylbenzyl)malononitrile (the present compound (27)).

Yield: 63%;
$^1$H-NMR (CDCl$_3$, TMS, δ (ppm)): 2.20–2.24 (2H, m), 2.48–2.63 (2H, m), 3.26 (2H, s), 5.32 (2H, d), 5.80 (2H, d), 6.72 (2H, dd), 7.33 (2H, d), 7.41 ( d).

PRODUCTION EXAMPLE 28

Using 0.20 g of (4-(trifluoromethoxy)benzyl)malononitrile, 5 ml of N,N-dimethylformamide, 50 mg of sodium hydride (60% in oil), and 0.17 ml of 1,1,3-trichloropropene, and according to the process described in the Production Example 1, there was obtained 80 mg of 2-(3,3-dichloro-2-propenyl)-2-(4-(trifluoromethoxy)benzyl)malononitrile (the present compound (28)).

Yield: 28%;
m.p.: 96.5° C.

PRODUCTION EXAMPLE 29

Using 0.20 g of (4-(trifluoromethoxy)benzyl)malononitrile, 5 ml of N,N-dimethylformamide, 50 mg of sodium hydride (60% in oil), and 0.46 g of 1,1,3-tribromopropene, and according to the process described in the Production Example 1, there was obtained 0.16 g of 2-(3,3-dibromo-2-propenyl)-2-(4-(trifluoromethoxy)benzyl)malononitrile (the present compound (29)).

Yield: 44%;
m.p.: 126.7° C.

PRODUCTION EXAMPLE 30

Using 0.23 g of 3-nitro-4-methylbenzyl bromide, 3 ml of N,N-di-methylformamide, 0.05 g of sodium hydride (60% in oil), and 0.17 g of (3,3,3-trifluoropropyl)malononitrile, and according to the process described in the Production Example 26, there was obtained 0.10 g of 2-(3-nitro-4-methylbenzyl)-2-(3,3,3-trifluoropropyl)malononitrile (the present compound (30)).

Yield: 31%;
$^1$H-NMR (CDCl$_3$, TMS, δ (ppm)): 2.25–2.30 (2H, m), 2.49–2.61 (2H, m), 2.65 (3H, s), 3.31 (2H, s), 7.45 (1H, d), 7.55 (1H, d), 8.00 (1H, s).

PRODUCTION EXAMPLE 31

Using 0.16 g of 4-ethylbenzyl chloride, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.14 g of 2-(4-ethylbenzyl)-2-(3,3,3-trifluoropropyl)malononitrile (the present compound (31)).

Yield: 50%;
$^1$H-NMR (CDCl$_3$, TMS, δ (ppm)): 1.25 (3H, t), 2.04–2.23 (2H, m), 2.50–2.58 (2H, m), 3.23 (2H, s), 7.24–7.28 (4H, m).

PRODUCTION EXAMPLE 32

Using 0.20 g of 3-methoxybenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.09 g of 2-(3-methoxybenzyl)-2-(3,3,3-trifluoropropyl)malononitrile (the present compound (32)).

Yield: 33%;
$^1$H-NMR (CDCl$_3$, TMS, δ (ppm)): 2.19–2.22 (2H, m), 2.48–2.59 (2H, m), 3.24 (2H, s), 3.83 (3H, s), 6.90–7.00 (3H, m), 7.31 (1H, m).

PRODUCTION EXAMPLE 33

Using 0.23 g of 4-t-butylbenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.14 g of 2-(4-t-butylbenzyl)-2-(3,3,3-trifluoropropyl)malononitrile (the present compound (33)).

Yield: 47%;

$^1$H-NMR (CDCl$_3$, TMS, δ (ppm)): 1.33 (9H, s), 2.20–2.24 (2H, m), 2.48–2.59 (2H, m), 3.24 (2H, s), 7.29 (2H, d), 7.43 (2H, d).

PRODUCTION EXAMPLE 34

Using 0.22 g of 4-(methylthio)benzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.15 g of 2-(4-(methylthio)benzyl)-2-(3,3,3-trifluoropropyl)malononitrile (the present compound (34)).

Yield: 50%;

$^1$H-NMR (CDCl$_3$, TMS, δ (ppm)): 2.17–2.22 (2H, m), 2.43–2.53 (2H, m), 2.50 (3H, s), 3.16 (2H, s), 7.29 (4H, s).

PRODUCTION EXAMPLE 35

Using 0.21 g of 4-isopropylbenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.24 g of 2-(4-isopropylbenzyl)-2-(3,3,3-trifluoropropyl)malononitrile (the present compound (35)).

Yield: 85%;

$^1$H-NMR (CDCl$_3$, TMS, δ (ppm)): 1.27 (6H, d), 2.20–2.23 (2H, m), 2.51–2.60 (2H, m), 3.36 (2H, s), 7.26 (4H, s).

PRODUCTION EXAMPLE 36

Using 0.24 g of 3-(trifluoromethyl)benzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.17 g of 2-(3-(trifluoromethyl)benzyl)-2-(3,3,3-trifluoropropyl)malononitrile (the present compound (36)).

Yield: 53%;

$^1$H-NMR (CDCl$_3$, TMS, δ (ppm)): 2.21–2.29 (2H, m), 2.48–2.62 (2H, m), 3.33 (2H, s), 7.52–7.72 (3H, m).

PRODUCTION EXAMPLE 37

Using 0.14 g of 3-metylbenzyl chloride, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.17 g of 2-(3-methylbenzyl)-2-(3,3,3-trifluoropropyl)malononitrile (the present compound (37)).

Yield: 62%;

$^1$H-NMR (CDCl$_3$, TMS, δ (ppm)): 2.18–2.23 (2H, m), 2.36 (3H, s), 2.47–2.59 (2H, m), 3.23 (2H, s), 7.16 (1H, s)7.22–7.33 (3H, m).

PRODUCTION EXAMPLE 38

Using 0.21 g of 2-chloro-4-nitrobenzyl chloride, 3 ml of N,N-di-methylformamide, 0.05 g of sodium hydride (60% in oil), and 0.17 g of (3,3,3-trifluoropropyl)malononitrile, and according to the process described in the Production Example 26, there was obtained 0.15 g of 2-(2-chloro-4-nitrobenzyl)-2-(3,3,3-trifluoropropyl)malononitrile (the present compound (38)).

Yield: 46%;

$^1$H-NMR (CDCl$_3$, TMS, δ (ppm)): 2.32–2.36 (2H, m), 2.49–2.60 (2H, m), 3.60 (2H, s), 7.60 (1H, d), 8.23 (1H, d), 8.39 (1H, s).

PRODUCTION EXAMPLE 39

Using 0.28 g of 3-chloro-4-(trifluoromethyl)benzyl chloride, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.25 g of 2-(3-chloro-4-(trifluoromethyl)benzyl)-2-(3,3,3-trifluoropropyl)malononitrile (the present compound (39)).

Yield: 70%;

$^1$H-NMR (CDCl$_3$, TMS, δ (ppm)): 2.26–2.30 (2H, m), 2.52–2.63 (2H, m), 3.28 (2H, s), 7.24 (1H, d), 7.29 (1H, d), 7.70 (1H, dd).

PRODUCTION EXAMPLE 40

Using 0.23 g of 2,3-dimethoxybenzyl bromide, 3 ml of N,N-di-methylformamide, 0.05 g of sodium hydride (60% in oil), and 0.17 g of (3,3,3-trifluoropropyl)malononitrile, and according to the process described in the Production Example 26, there was obtained 0.26 g of 2-(2,3-dimethoxybenzyl)-2-(3,3,3-trifluoropropyl)malononitrile (the present compound (40)).

Yield: 80%;

$^1$H-NMR (CDCl$_3$, TMS, δ (ppm)): 2.18–2.22 (2H, m), 2.46–2.57 (2H, m), 3.37 (2H, s), 3.88 (3H, s), 3.90 (3H, s), 6.95–7.11 (2H, d).

PRODUCTION EXAMPLE 41

Using 0.10 g of 2-chloro-4-(trifluoromethyl)benzyl bromide, 3 ml of N,N-dimethylformamide, 0.05 g of sodium hydride (60% in oil), and. 0.17 g of (3,3,3-trifluoropropyl)malononitrile, and according to the process described in the Production Example 26, there was obtained 0.05 g of 2-(2-chloro-4-(trifluoromethyl)benzyl)-2-(3,3,3-trifluoropropyl)malononitrile (the present compound (41)).

Yield: 39%;

$^1$H-NMR (CDCl$_3$, TMS, δ (ppm)): 2.21–2.35 (2H, m), 2.49–2.63 (2H, m), 3.56 (2H, s), 7.62 (1H, d), 7.68 (1H, d), 7.78 (1H, s).

PRODUCTION EXAMPLE 42

Using 2.05 g of 2-(1-(4-chlorophenyl)ethyl)malononitrile, 10 ml of N,N-dimethylformamide, 1.38 g of potassium carbonate, and 1.77 g of 1-bromo-3,3,3-trifluoropropane, and according to the process described in the Production Example 1, there was obtained 0.49 g of 2-(1-(4-chlorophenyl)ethyl)-2-(3,3,3-trifluoropropyl)malononitrile (the present compound (42)).

Yield: 17%;

$^1$H-NMR (CDCl$_3$, TMS, δ (ppm)): 1.71 (3H, d), 1.86–2.14 (2H,m), 2.40–2.60 (2H,m), 3.22 (1H,q), 7.27 (2H,d), 7.39 (2H,d).

PRODUCTION EXAMPLE 43

First, 1.00 g of 2-(3,3,3-trifluoropropyl)-2-(4-vinylbenzyl)malononitrile (the present compound (27)) was dissolved in 10 ml of chloroform, to which 0.5 g of bromine dissolved in 8 ml of chloroform was added dropwise slowly, while stirring under ice cooling, followed by further stirring for 5 hours. Then, water was added to the reaction mixture, which was extracted with chloroform. The organic layer was successively washed with water and a saturated aqueous sodium chloride solution, dried over anhydrous magnesium sulfate, and then concentrated under reduced pressure. The residue was subjected to silica gel column chromatography to give 1.07 g of 2-(4-(1,2-dibromoethyl)benzyl)-2-(3,3,3-trifluoropropyl)malononitrile (the present compound (43)).

Yield: 68%;
$^1$H-NMR (CDCl$_3$, TMS, δ (ppm)): 2.22–2.26 (2H, m), 2.49–2.61 (2H, m), 3.27 (2H, s), 3.97 (1H, t), 4.07 (1H, dd), 5.14 (1H, dd), 7.39 (2H, d), 7.48 (2H, d).

PRODUCTION EXAMPLE 44

Using 0.51 g of (2-chloro-4-fluorobenzyl)malononitrile, 5 ml of N,N-dimethylformamide, 0.12 g of sodium hydride (60% in oil), and 0.34 g of 1-bromo-3,3,3-trifluoropropane, and according to the process described in the Production Example 1, there was obtained 0.21 g of 2-(2-chloro-4-fluorobenzyl)-2-(3,3,3-trifluoropropyl)malononitrile (the present compound (44)).

Yield: 34%;
$^1$H-NMR (CDCl$_3$, TMS, δ (ppm)): 2.27–2.31 (2H, m), 2.50–2.62 (2H, m), 3.48 (2H, s), 7.07 (1H, m), 7.26 (1H, m), 7.53 (1H, m).

PRODUCTION EXAMPLE 45

Using 0.49 g of 3-metyl-4-nitrobenzyl methanesulfonate, 5 ml of N,N-dimethylformamide, 0.10 g of sodium hydride (60% in oil), and 0.3 g of (3,3,3-trifluoropropyl)malononitrile, and according to the process described in the Production Example 26, there was obtained 0.51 g of 2-(3-methyl-4-nitrobenzyl)-2-(3,3,3-trifluoropropyl)malononitrile (the present compound (45)).

Yield: 82%;
$^1$H-NMR (CDCl$_3$, TMS, δ (ppm)): 2.14–2.30 (2H, m), 2.51–2.65 (2H, m), 2.66 (3H, s), 7.37 (1H, d), 7.39 (1H, d), 8.03 (1H, dd).

PRODUCTION EXAMPLE 46

Using 0.32 g of (4-cyanobenzyl)malononitrile, 7 ml of N,N-di-methylformamide, 0.12 g of sodium hydride (60% in oil), and 0.25 g of 1-bromo-2-fluoroethane, and according to the process described in the Production Example 1, there was obtained 0.10 g of 2-(4-cyanobenzyl)-2-(2-fluoroethyl)malononitrile (the present compound (46)).

Yield: 22%;
$^1$H-NMR (CDCl$_3$, TMS, δ (ppm)): 2.45 (2H, dt), 3.36 (2H, s), 4.85 (2H, dt), 7.55 (2H, d), 7.75 (2H, d).

PRODUCTION EXAMPLE 47

Using 0.40 g of (4-nitrobenzyl)malononitrile, 5 ml of N,N-dimethylformamide, 0.12 g of sodium hydride (60% in oil), and 0.25 g of 1-bromo-2-fluoroethane, and according to the process described in the Production Example 1, there was obtained 0.10 g of 2-(4-nitrobenzyl)-2-(2-fluoroethyl)malononitrile (the present compound (47)).

Yield: 22%;
$^1$H-NMR (CDCl$_3$, TMS, δ (ppm)): 2.47 (2H, dt), 3.41 (2H, s), 4.86 (2H, dt), 7.61 (2H, d), 8.30 (2H, d).

PRODUCTION EXAMPLE 48

Using 0.50 g of (4-(trifluoromethoxy)benzyl)malononitrile, 9 ml of N,N-dimethylformamide, 96 mg of sodium hydride (60% in oil), and 0.79 g of 4-bromo-1,1,2-trifluoro-1-butene, and according to the process described in the Production Example 1, there was obtained 0.19 g of 2-(3,4,4-trifluoro-3-butenyl)-2-(4-(trifluoromethoxy)benzyl)malononitrile (the present compound (49)).

Yield: 27%;
$^1$H-NMR (CDCl$_3$, TMS, δ (ppm)): 2.19–2.26(2H, m), 2.66–2.81(2H, m), 3.26(2H, s), 7.28(2H, d), 7.43(2H, d).

PRODUCTION EXAMPLE 49

Using 0.50 g of (4-(trifluoromethoxy)benzyl)malononitrile, 8 ml of N,N-dimethylformamide, 96 mg of sodium hydride (60% in oil), and 0.74 g of 1-bromo-3,3,3-trifluoropropane, and according to the process described in the Production Example 1, there was obtained 0.14 g of 2-(3,3,3-trifluoropropyl)-2-(4-(trifluoromethoxy)benzyl)malononitrile (the present compound (50)).

Yield: 21%;
$^1$H-NMR (CDCl$_3$, TMS, δ (ppm)): 2.21–2.28 (2H, m), 2.46–2.61 (2H, m), 3.27 (2H, s), 7.27 (2H, d), 7.44 (2H, d).

PRODUCTION EXAMPLE 50

Using 0.47 g of (4-bromobenzyl)malononitrile, 5 ml of N,N-di-methylformamide, 0.12 g of sodium hydride (60% in oil), and 0.25 g of 1-bromo-2-fluoroethane, and according to the process described in the Production Example 1, there was obtained 0.27 g of 2-(4-bromobenzyl)-2-(2-fluoroethyl)malononitrile (the present compound (51)).

Yield: 48%;
$^1$H-NMR (CDCl$_3$, TMS, δ (ppm)): 2.39 (2H, dt), 3.26 (2H, s), 4.83 (2H, dt), 7.22 (2H, d), 7.55 (2H, d).

PRODUCTION EXAMPLE 51

Using 0.37 g of (4-methoxybenzyl)malononitrile, 5 ml of N,N-dimethylformamide, 0.12 g of sodium hydride (60% in oil), and 0.25 g of 1-bromo-2-fluoroethane, and according to the process described in the Production Example 1, there was obtained 0.23 g of 2-(2-fluoroethyl)-2-(4-methoxybenzyl)malononitrile (the present compound (52)).

Yield: 49%;
$^1$H-NMR (CDCl$_3$, TMS, δ (ppm)): 2.35 (2H, dt), 3.22 (2H, s), 3.76 (3H, s), 4.80 (2H, dt), 6.91 (2H, d), 7.28 (2H, d).

PRODUCTION EXAMPLE 52

Using 0.41 g of 2-(1-(4-chlorophenyl)ethyl)malononitrile, 5 ml of N,N-dimethylformamide, 0.12 g of sodium hydride (60% in oil), and 0.25 g of 1-bromo-2-fluoroethane, and according to the process described in the Production Example 1, there was obtained 0.22 g of 2-(1-(4-chlorophenyl)ethyl)-2-(2-fluoroethyl)malononitrile (the present compound (53)).

Yield: 44%;
¹H-NMR (CDCl₃, TMS, δ (ppm)): 1.71 (3H, d), 2.04–2.33 (2H, m)3.30 (1H, q), 4.80 (2H, dt), 7.28 (2H, d), 7.37 (2H, d).

PRODUCTION EXAMPLE 53

Using 0.50 g of (4-(trifluoromethylthio)benzyl)malononitrile, 10 ml of N,N-dimethylformamide, 86 mg of sodium hydride (60% in oil), and 0.74 g of 4-bromo-1,1,2-trifluoro-1-butene, and according to -the process described in the Production Example 1, there was obtained 0.12 g of 2-(3,4,4-trifluoro-3-butenyl)-2-(4-(trifluoromethylthio)benzyl)malononitrile (the present compound (54)).
Yield: 17%;
¹H-NMR (CDCl₃, TMS, δ (ppm)): 2.20–2.27 (2H, m), 2.68–2.82 (2H, m), 3.28 (2H, s), 7.45 (2H, d), 7.72 (2H, d).

PRODUCTION EXAMPLE 54

Using 0.45 g of (4-(trifluoromethyl)benzyl)malononitrile, 5 ml of N,N-dimethylformamide, 0.12 g of sodium hydride (60% in oil), and 0.25 g of 1,1,3-trichloropropene, and according to the process described in the Production Example 1, there was obtained 0.28 g of 2-(3,3-dichloro-2-propenyl)-2-(4-(trifluoromethyl)benzyl)malononitrile (the present compound (55)).
Yield: 37%;
¹H-NMR (CDCl₃, TMS, δ (ppm)): 2.96 (2H, d), 3.28 (2H, s), 6.09 (1H, d), 7.53 (2H, d), 7.70 (2H, d).

PRODUCTION EXAMPLE 55

Using 0.37 g of (4-cyanobenzyl)malononitrile, 5 ml of N,N-dimethylformamide, 0.12 g of sodium hydride (60% in oil), and 0.25 g of 1,3,3-trichloropropene, and according to the process described in the Production Example 1, there was obtained 0.17 g of 2-(4-cyanobenzyl)-2-(3,3-dichloropropenyl)malononitrile (the present compound (56)).
Yield: 29%;
¹H-NMR (CDCl₃, TMS, δ (ppm)): 2.97 (2H, d), 3.24 (2H, s), 6.08 (1H, d), 7.53 (2H, d), 7.64 (2H, d).

PRODUCTION EXAMPLE 56

Using 0.48 g of 2-(1-(4-(trifluoromethyl)phenyl)ethyl)malononitrile, 5 ml of N,N-dimethylformamide, 0.12 g of sodium hydride (60% in oil), and 0.34 g of 1-bromo-3,3,3-trifluoropropane, and according to the process described in the Production Example 1, there was obtained 0.26 g of 2-(1-(4-(trifluoromethyl)phenyl)ethyl-2-(3,3,3-trifluoropropyl)malononitrile (the present compound (57)).
Yield: 39%;
¹H-NMR (CDCl₃, TMS, δ (ppm)): 1.76 (3H, d), 1.90–2.23 (2H, m), 2.43–2.96 (2H, m), 3.32 (1H, q), 7.48 (2H, d), 7.71 (2H, d).

PRODUCTION EXAMPLE 57

First, 0.2 g of (2-(4-(1,2-dibromoethyl)benzyl)-2-(3,3,3-trifluoropropyl)malononitrile (the present compound (43)) was dissolved in 5 ml of N,N-dimethylformamide, to which 0.1 g of potassium t-butoxide was added, while stirring under ice cooling. After stirring for 5 hours at room temperature, water was added to the reaction mixture, which was extracted with ethyl acetate. The organic layer was successively washed with water, a saturated aqueous sodium chloride solution, dried over anhydrous magnesium sulfate, and then concentrated under reduced pressure. The residue was subjected to silica gel column chromatography to give 0.05 g of 2-(4-(2-bromovinyl)benzyl)-2-(3,3,3-trifluoropropyl)malononitrile (the present compound (58)).
Yield: 41%;
¹H-NMR (CDCl₃, TMS, δ (ppm)): 2.20–2.26 (2H, m), 2.49–2.61 (2H, m), 3.27 (2H, s), 3.51 (2H, s), 5.84 (1H, d), 6.17 (1H, d), 7.34 (2H, d), 7.68 (2H, d).

PRODUCTION EXAMPLE 58

Using 0.37 g of (4-fluorobenzyl)malononitrile, 5 ml of N,N-dimethylformamide, 0.12 g of sodium hydride (60% in oil), and 0.25 g of 1-bromo-2-fluoroethane, and according to the process described in the Production Example 1, there was obtained 0.22 g of 2-(4-fluorobenzyl)-2-(2-fluoroethyl)malononitrile (the present compound (59)).
Yield: 49%;
¹H-NMR (CDCl₃, TMS, δ (ppm)): 2.40 (2H, dt), 3.28 (2H, s), 4.83 (2H, dt), 7.04–7.14 (2H, m), 7.36–7.40 (2H, m).

PRODUCTION EXAMPLE 59

Using 0.49 g of benzylmalononitrile, 15 ml of N,N-dimethylformamide, 0.14 g of sodium hydride (60% in oil), and 0.33 g of 1,3-dichloropropene, and according to the process described in the Production Example 1, there was obtained 0.25 g of 2-benzyl-2-((E)-3-chloro-2-propenyl)malononitrile (the present compound (60)) as high-polar compound.
Yield: 36%;
¹H-NMR (CDCl₃, TMS, δ (ppm)): 2.71 (2H, d), 3.21 (2H, s), 6.06 (1H, dt), 6.37 (1H, d), 7.36–7.45 (5H, m).
And there was obtained 0.28 g of 2-benzyl-2-((Z)-3-chloro-2-propenyl)malononitrile (the present compound (61)) as low-polar compound.
Yield: 40%;
¹H-NMR (CDCl₃, TMS, δ (ppm)): 2.98 (2H, d), 3.26 (2H, s), 6.00 (1H, dt), 6.49 (1H, d), 7.37–7.52 (5H, m).

PRODUCTION EXAMPLE 60

Using 0.30 g of (3,4,4-trifluoro-3-butenyl)malononitrile, 5 ml of N,N-dimethylformamide, 75 mg of sodium hydride (60% in oil), and 0.52 g of 2-chloro-4-(trifluoromethyl)benzylbromide, and according to the process described in the Production Example 1, there was obtained 0.28 g of 2-(2-chloro-4-(trifluoromethyl)benzyl)-2-(3,4,4-trifluoro-3-butenyl)malononitrile (the present compound (62)).
Yield: 45%;
¹H-NMR (CDCl₃, TMS, δ (ppm)): 2.30 (2H, t), 2.66–2.88 (2H, m), 3.56 (2H, s), 7.63 (1H, d), 7.70 (1H, d), 7.75 (1H, s).

PRODUCTION EXAMPLE 61

Using 1.01 g of (3-chlorobenzyl)malononitrile, 5 ml of N,N-dimethylformamide, 1.38 g of potassium carbonate, and 1.44 g of 1-bromo-2-chloroethane, and according to the process described in the Production Example 1, there was obtained 0.60 g of 2-(3-chlorobenzyl)-2-(2-chloroethyl)malononitrile (the present compound (63)).
Yield: 23%;
¹H-NMR (CDCl₃, TMS, δ (ppm)): 2.44 (2H, dd), 3.25 (2H, s), 3.81 (2H, dd), 7.27–7.43 (4H, m).

PRODUCTION EXAMPLE 62

Using 0.23 g of (4-(trifluoromethyl)benzyl)malononitrile, 3 ml of N,N-dimethylformamide, 0.05 g of sodium hydride (60% in oil), and 0.13 g of 1-bromo-2-fluoroethane, and according to the process described in the Production Example 1, there was obtained 0.12 g of 2-(2-fluoroethyl)-2-(4-(trifluoromethyl)benzyl)malononitrile (the present compound (64)).

Yield: 48%;

$^1$H-NMR (CDCl$_3$, TMS, δ (ppm)): 2.43 (2H, dt), 3.58 (2H, s), 4.85 (2H, dt), 7.54 (2H, d), 7.70 (2H, d).

PRODUCTION EXAMPLE 63

Using 0.24 g of (3-bromobenzyl)malononitrile, 3 ml of N,N-dimethylformamide, 0.10 g of sodium hydride (60% in oil), and 0.13 g of 1-bromo-2-fluoroethane, and according to the process described in the Production Example 1, there was obtained 0.11 g of 2-(3-bromobenzyl)-2-(2-fluoroethyl)malononitrile (the present compound (65)).

Yield: 33%;

$^1$H-NMR (CDCl$_3$, TMS, δ (ppm)): 2.38 (2H, dt), 3.26 (2H, s), 3.83 (3H, s), 4.86 (2H, dt), 7.27–7.37 (2H, m)7.54–7.57 (2H, m).

PRODUCTION EXAMPLE 64

Using 0.15 g of (3,4,4-trifluoro-3-butenyl)malononitrile, 5 ml of N,N-dimethylformamide, 38 mg of sodium hydride (60% in oil), and 0.27 g of 2,6-dichloro-4-(trifluoromethyl)benzylbromide, and according to the process described in the Production Example 1, there was obtained 0.18 g of 2-(2,6-dichloro-4-(trifluoromethyl)benzyl)-2-(3,4,4-trifluoro-3-butenyl)malononitrile (the present compound (66)).

Yield: 51%;

$^1$H-NMR (CDCl$_3$, TMS, δ (ppm)): 2.39–2.45 (2H, m), 2.71–2.83 (2H, m), 3.80 (2H, s), 7.70 (2H, s).

PRODUCTION EXAMPLE 65

Using 0.25 g of (4-bromo-2-fluorobenzyl)malononitrile, 3 ml of N,N-dimethylformamide, 0.10 g of sodium hydride (60% in oil), and 0.13 g of 1-bromo-2-fluoroethane, and according to the process described in the Production Example 1, there was obtained 0.10 g of 2-(4-bromo-2-fluorobenzyl)-2-(2-fluoroethyl)malononitrile (the present compound (67)).

Yield: 33%;

$^1$H-NMR (CDCl$_3$, TMS, δ (ppm)): 2.41 (2H, dt), 3.35 (2H, s), 4.82 (2H, dt), 7.32–7.42 (3H, m).

PRODUCTION EXAMPLE 66

Using 0.20 g of (3,4,4-trifluoro-3-butenyl)malononitrile, 5 ml of N,N-dimethylformamide, 50 mg of sodium hydride (60% in oil), and 0.25 g of α-bromo-p-tolunitrile, and according to the process described in the Production Example 1, there was obtained 0.21 g of 2-(4-cyanobenzyl)-2-(3,4,4-trifluoro-3-butenyl)malononitrile (the present compound (68)).

Yield: 63%;

$^1$H-NMR (CDCl$_3$, TMS, δ (ppm)): 2.21–2.32 (2H, m), 2.68–2.87 (2H, m), 3.31 (2H, s), 7.54 (2H, d), 7.72 (2H, d).

PRODUCTION EXAMPLE 67

Using 0.24 g of (2-bromobenzyl)malononitrile, 3 ml of N,N-dimethylformamide, 0.10 g of sodium hydride (60% in oil), and 0.13 g of 1-bromo-2-fluoroethane, and according to the process described in the Production Example 1, there was obtained 0.12 g of 2-(2-bromobenzyl)-2-(2-fluoroethyl)malononitrile (the present compound (69)).

Yield: 37%;

$^1$H-NMR (CDCl$_3$, TMS, δ (ppm)): 2.47 (2H, dt), 3.58 (2H, s), 4.82 (2H, dt), 7.24 (1H, dd), 7.28 (1H, dd), 7.58 (1H, d), 7.65 (1H, d).

PRODUCTION EXAMPLE 68

Using 0.21 g of 2,4-difluorobenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.17 g of 2-(2,4-difluorobenzyl)-2-(3,3,3-trifluoropropyl)malononitrile (the present compound (70)).

Yield: 57%;

$^1$H-NMR (CDCl$_3$, TMS, δ (ppm)): 2.21–2.26 (2H, m), 2.47–2.59 (2H, m), 3.34 (2H, s), 6.91–7.02 (2H, m), 7.40–7.47 (2H, m).

PRODUCTION EXAMPLE 69

Using 0.21 g of 3,5-difluorobenzyl bromide, 3 ml of N,N-dimethyl-formamide, 0.05 g of sodium hydride (60% in oil), and 0.17 g of (3,3,3-trifluoropropyl)malononitrile, and according to the process described in the Production Example 26, there was obtained 0.21 g of 2-(3,5-difluorobenzyl)-2-(3,3,3-trifluoropropyl)malononitrile (the present compound (71)).

Yield: 73%;

$^1$H-NMR (CDCl$_3$, TMS, δ (ppm)): 2.22–2.28 (2H, m), 2.49–2.61 (2H, m), 3.23 (2H, s), 6.87–6.95 (3H, m).

PRODUCTION EXAMPLE 70

Using 1.0 g of (4-(trifluoromethyl)benzyl)malononitrile, 8 ml of N,N-dimethylformamide, 0.73 g of cesium carbonate, and 1.0 g of 2,2,2-trifluoroethyl trifluoromethanesulfonate, and according to the process described in the Production Example 1, there was obtained 0.58 g of 2-(2,2,2-trifluoroethyl)-2-(4-(trifluoromethyl)benzyl)malononitrile (the present compound (72)).

Yield: 40%;

$^1$H-NMR (CDCl$_3$, TMS, δ (ppm)): 2.84 (2H, q), 3.40 (2H, d), 7.55 (2H, d), 7.72 (2H, d).

PRODUCTION EXAMPLE 71

Using 0.50 g of (4-(trifluoromethyl)benzyl)malononitrile, 6 ml of N,N-dimethylformamide, 98 mg of sodium hydride (60% in oil), and 0.46 g of 4-bromo-1,1,2-trifluoro-1-butene, and according to the process described in the Production Example 1, there was obtained 0.16 g of 2-(3,4,4-trifluoro-3-butenyl)-2-(4-(trifluoromethyl)benzyl)malononitrile (the present compound (73)).

Yield: 21%;

$^1$H-NMR (CDCl$_3$, TMS, δ (ppm)): 2.21–2.27 (2H, m), 2.70–2.79 (2H, m), 3.31 (2H, s), 7.52 (2H, d), 7.71 (2H, d).

PRODUCTION EXAMPLE 72

Using 0.50 g of (4-(trifluoromethyl)benzyl)malononitrile, 6 ml of N,N-dimethylformamide, 98 mg of sodium hydride (60% in oil), and 0.43 g of 1-bromo-3,3,3-trifluoropropane, and according to the process described in the Production Example 1, there was obtained 0.30 g of 2-(3,3,3-trifluoropropyl)-2-(4-(trifluoromethyl)benzyl)malononitrile (the present compound (74)).

Yield: 40%;

$^1$H-NMR (CDCl$_3$, TMS, δ (ppm)): 2.23–2.30 (2H, m), 2.47–2.66 (2H, m), 3.32 (2H, s), 7.52 (2H, d), 7.71 (2H, d).

PRODUCTION EXAMPLE 73

Using 0.19 g of 2-fluorobenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.17 g of 2-(2-fluorobenzyl)-2-(3,3,3-trifluoropropyl)malononitrile (the present compound (75)).

Yield: 63%;

$^1$H-NMR (CDCl$_3$, TMS, δ (ppm)): 2.20–2.26 (2H, m), 2.46–2.62 (2H, m), 3.38 (2H, s), 7.14–7.45 (4H, m).

PRODUCTION EXAMPLE 74

Using 0.50 g of (4-(trifluoromethyl)benzyl)malononitrile, 5 ml of N,N-dimethylformamide, 363 mg of cesium carbonate, and 0.63 g of 2,2,3,3,3-pentafluoropropyl trifluoromethanesulfonate, and according to the process described in the Production Example 1, there was obtained 0.20 g of 2-(2,2,3,3,3-pentafluoropropyl)-2-(4-(trifluoromethyl)benzyl)malononitrile (the present compound (76)).

Yield: 34%;

$^1$H-NMR (CDCl$_3$, TMS, δ (ppm)): 2.78 (2H, t), 3.43 (2H, s), 7.56 (2H, d), 7.75 (2H, d).

PRODUCTION EXAMPLE 75

Using 0.50 g of (4-(trifluoromethyl)benzyl)malononitrile, 5 ml of N,N-dimethylformamide, 59 mg of sodium hydride (60% in oil), and 0.77 g of 2,2,3,3,4,4,4-heptafluorobutyl trifluoromethanesulfonate, and according to the process described in the Production Example 1, there was obtained 73 mg of 2-(2,2,3,3,4,4,4-heptafluorobutyl)-2-(4-(trifluoromethyl)benzyl)malononitrile (the present compound (77)).

Yield: 8%;

$^1$H-NMR (CDCl$_3$, TMS, δ (ppm)): 2.82 (2H, t), 3.43 (2H, s), 7.56 (2H, d), 7.73 (2H, d).

PRODUCTION EXAMPLE 76

Using 0.50 g of (4-(trifluoromethyl)benzyl)malononitrile, 5 ml of N,N-dimethylformamide, 88 mg of sodium hydride (60% in oil), and 0.53 g of 1-iodo-4,4,4-trifluorobutane, and according to the process described in the Production Example 1, there was obtained 0.25 g of 2-(4,4,4-trifluorobutyl)-2-(4-(trifluoromethyl)benzyl)malononitrile (the present compound (78)).

Yield: 30%;

$^1$H-NMR (CDCl$_3$, TMS, δ (ppm)): 1.99–2.39 (4H, m), 2.18–2.24 (2H, m), 3.26 (2H, s), 7.49 (2H, d), 7.67 (2H, d).

PRODUCTION EXAMPLE 77

Using 0.15 g of 3-fluorobenzyl chloride, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.11 g of 2-(3-fluorobenzyl)-2-(3,3,3-trifluoropropyl)malononitrile (the present compound (79)).

Yield: 41%;

$^1$H-NMR (CDCl$_3$, TMS, δ (ppm)): 2.21–2.26 (2H, m), 2.47–2.57 (2H, m), 3.26 (2H, s), 7.08–7.18 (3H, m), 7.38–7.45 (1H, m).

PRODUCTION EXAMPLE 78

Using 0.26 g of 2,3,4,5,6-pentafluoaobenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.21 g of 2-(2,3,4,5,6-pentafluorobenzyl)-2-(3,3,3-trifluoropropyl)malononitrile (the present compound (80)).

Yield: 61%;

$^1$H-NMR (CDCl$_3$, TMS, δ (ppm)): 2.28–2.34 (2H, m), 2.50–2.68 (2H, m), 3.47 (2H, s).

PRODUCTION EXAMPLE 79

Using 0.21 g of 2-chlorobenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.22 g of 2-(2-chlorobenzyl)-2-(3,3,3-trifluoropropyl)malononitrile (the present compound (81)).

Yield: 78%;

$^1$H-NMR (CDCl$_3$, TMS, δ (ppm)): 2.28–2.34(2H, m), 2.50–2.62(2H, m), 3.53(2H, s), 7.30–7.40(2H, m), 7.47–7.55(2H, m).

PRODUCTION EXAMPLE 80

Using 0.16 g of 3-chlorobenzyl chloride, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.12 g of 2-(3-chlorobenzyl)-2-(3,3,3-trifluoropropyl)malononitrile (the present compound (82)).

Yield: 42%;

$^1$H-NMR (CDCl$_3$, TMS, δ (ppm)): 2.26–2.31 (2H, m), 2.47–2.62 (2H, m), 3.53 (2H, s), 7.26–7.55 (4H, m).

PRODUCTION EXAMPLE 81

Using 0.20 g of 2,4-dichlorobenzyl chloride, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.23 g of 2-(2,4-dichlorobenzyl)-2-(3,3,3-trifluoropropyl)malononitrile (the present compound (83)).

Yield: 70%;

$^1$H-NMR (CDCl$_3$, TMS, δ (ppm)): 2.26–2.31 (2H, m), 2.48–2.63 (2H, m), 3.48 (2H, s), 7.35 (1H, dd), 7.47 (1H, d), 7.52 (1H, d).

PRODUCTION EXAMPLE 82

Using 0.19 g of 4-methylbenzyl bromide, 3 ml of N,N-dimethylformamide, 0.05 g of sodium hydride (60% in oil), and 0.17 g of (3,3,3-trifluoropropyl)malononitrile, and according to the process described in the Production Example 26, there was obtained 0.20 g of 2-(4-methylbenzyl)-2-(3,3,3-trifluoropropyl)malononitrile (the present compound (84)).

Yield: 76%;
$^1$H-NMR (CDCl$_3$, TMS, δ (ppm)): 2.17–2.27(2H, m), 2.38(3H, 1H), 2.48–2.60(2H, m), 3.23(2H, s), 7.21–7.27(4H, m).

PRODUCTION EXAMPLE 83

Using 0.22 g of (4-(trifluoromethyl)benzyl)malononitrile, 3 ml of N,N-dimethylformamide, 0.05 g of sodium hydride (60% in oil), and 0.31 g of 1-bromo-3-chloropropane, and according to the process described in the Production Example 1, there was obtained 0.15 g of 2-(3-chloropropyl)-2-(4-(trifluoromethyl)benzyl)malononitrile (the present compound (85)).

Yield: 26%;
$^1$H-NMR (CDCl$_3$, TMS, δ (ppm)): 2.20–2.26(4H, m), 3.26(2H, d), 3.68(2H, dd), 7.51(2H, d), 7.69(2H, d).

PRODUCTION EXAMPLE 84

Using 0.22 g of 2-(4-(trifluoromethyl)benzyl)malononitrile, 3 ml of N,N-dimethylformamide, 0.05 g of sodium hydride (60% in oil), and 0.33 g of 1-bromo-3-chloro-2-methylpropane, and according to the process described in the Production Example 1, there was obtained 0.19 g of 2-(3-chloro-2-methylpropyl)-2-(4-(trifluoromethyl)benzyl)malononitrile (the present compound (86)).

Yield: 30%;
$^1$H-NMR (CDCl$_3$, TMS, δ (ppm)): 1.45(3H, d), 1.94(1H, dd), 2.31(1H, dd), 2.36–2.43(1H, m), 3.29(2H, s), 3.52(1H, dd), 3.68(1H, dd), 7.53(2H, d), 7.69(2H, d).

PRODUCTION EXAMPLE 85

Using 0.22 g of (4-(trifluoromethyl)benzyl)malononitrile, 3 ml of N,N-dimethylformamide, 0.05 g of sodium hydride (60% in oil), and 0.34 g of 1-bromo-4-chlorobutane, and according to the process described in the Production Example 1, there was obtained 0.20 g of 2-(4-chlorobutyl)-2-(4-(trifluoromethyl)benzyl)malononitrile (the present compound (87)).

Yield: 32%;
$^1$H-NMR (CDCl$_3$, TMS, δ (ppm)): 1.92–2.14(4H, m), 3.27(2H, s), 2.36–2.43(1H, m), 3.29(2H, s), 3.57(2H, dd), 7.52(2H, d), 7.69(2H, d).

PRODUCTION EXAMPLE 86

Using 0.52 g of (3-benzyloxybenzyl)malononitrile, 5 ml of N,N-dimethylformamide, 0.12 g of sodium hydride (60% in oil), and 0.34 g of 1-bromo-3,3,3-trifluoropropane, and according to the process described in the Production Example 1, there was obtained 0.28 g of 2-(3-(benzyloxy)benzyl)-2-(3,3,3-trifluoropropyl)malononitrile (the present compound (88)).

Yield: 38%;
$^1$H-NMR (CDCl$_3$, TMS, δ (ppm)): 2.05–2.22(2H, m), 2.47–2.59(2H, m), 3.24(1H, q), 5.09(2H, s), 6.95–7.26(3H, m), 7.29–7.52(6H, m).

PRODUCTION EXAMPLE 87

Using 0.39 g of 2-(4-methoxybenzyl)malononitrile, 5 ml of N,N-dimethylformamide, 0.12 g of sodium hydride (60% in oil), and 0.34 g of 1-bromo-3,3,3-trifluoropropane, and according to the process described in the Production Example 1, there was obtained 0.15 g of 2-(4-methoxybenzyl)-2-(3,3,3-trifluoropropyl)malononitrile (the present compound (89)).

Yield: 27%;
$^1$H-NMR (CDCl$_3$, TMS, δ (ppm)): 2.04–2.22(2H, m), 2.46–2.63(2H, m), 3.79(1H, q), 3.83(3H, s), 6.92(2H, d), 7.27(2H, d).

The following will describe some production examples for intermediate compounds as reference production examples.

REFERENCE PRODUCTION EXAMPLE 1

First, 1.00 g of (4-chloro-α-methylbenzylidene)malononitrile of the formula:

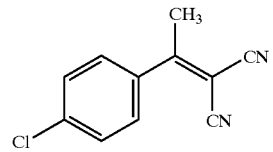

was dissolved in 20 ml of diethyl ether, to which a catalytic amount of copper (I) iodide was added, and while stirring under ice cooling, a solution of methyl magnesium iodide in diethyl ether (prepared from 0.30 g of magnesium, 10 ml of diethyl ether, and 0.86 ml of methyl iodide) was added dropwise, followed by stirring for 30 minutes under ice cooling. Then, 10% hydrochloric acid was added to the reaction mixture, which was extracted with ethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 0.74 g of (1-(4-chlorophenyl)-1-methylethyl)malononitrile (the intermediate (2)).

Yield: 69%.

REFERENCE PRODUCTION EXAMPLE 2

First, 1.02 g of (4-chlorobenzylidene)malononitrile was dissolved in 20 ml of tetrahydrofuran, to which a catalytic amount of copper (I) iodide was added, and while stirring under ice cooling, a solution of isopropyl magnesium bromide in tetrahydrofuran (prepared from 0.34 g of magnesium, 10 ml of tetrahydrofuran, and 1.46 ml of isopropyl bromide) was added dropwise, followed by stirring for 30 minutes under ice cooling. Then, 10% hydrochloric acid was added to the reaction mixture, which became acidic and was extracted with ethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 0.66 g of (1-(4-chlorophenyl)-2-methylpropyl)malononitrile (the intermediate (3)).

Yield: 52%.

REFERENCE PRODUCTION EXAMPLE 3

First, 4.44 g of (4-(trifluoromethyl)benzylidene)malononitrile was dissolved in 20 ml of ethanol, and while stirring at room temperature, a suspension of 0.19 g of sodium borohydride in 5 ml of ethanol was added dropwise, followed by stirring at room temperature for 30 minutes. Then, 10% hydrochloride acid was added to the reaction mixture, which became acidic and was extracted with diethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 2.30 g of (4-(trifluoromethyl)benzyl)malononitrile (the intermediate (4)).

Yield: 51%.

REFERENCE PRODUCTION EXAMPLE 4

First, 3.00 g of (4-chloro-α-methylbenzylidene)malononitrile was dissolved in 20 ml of ethanol, and while stirring at room temperature, a suspension of 0.15 g of sodium borohydride in 5 ml of ethanol was added dropwise, followed by stirring at room temperature for 30 minutes. Then, 10% hydrochloride acid was added to the reaction mixture, which was extracted with diethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 1.70 g of (1-(4-chlorophenyl)ethyl)malononitrile (the intermediate (6)).

Yield: 56%.

REFERENCE PRODUCTION EXAMPLE 5

First, 10.0 g of 4-(trifluoromethoxy)benzaldehyde and 3.50 g of malononitrile were dissolved in 60 ml of 70% (w/w) aqueous ethanol, to which a catalytic amount of benzyltrimethylammonium hydroxide was added, and the mixture was stirred at room temperature overnight. Then, a saturated aqueous sodium chloride solution was added to the reaction mixture, which was extracted with ethyl acetate. The organic layer was washed with a saturated aqueous sodium chloride solution, dried over anhydrous magnesium sulfate, and then concentrated under reduced pressure. The residue was recrystallized from t-butyl methyl ether and hexane to give 9.24 g of (4-(trifluoromethoxy)benzylidene)malononitrile.

Yield: 74%;

$^1$H-NMR (CDCl$_3$, TMS, δ (ppm)): 7.37 (2H, d), 7.76 (1H, s), 7.98 (2H, d).

Then, 2.61 g of (4-(trifluoromethoxy)benzylidene)malononitrile was dissolved in 20 ml of tetrahydrofuran, and while stirring at room temperature, a suspension of 0.11 g of sodium borohydride in 5 ml of ethanol was added dropwise, followed by stirring at room temperature for 30 minutes. Then, 10% hydrochloric acid was added, and the mixture was extracted with diethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 2.20 g of (4-(trifluoromethoxy)benzyl)malononitrile (the intermediate (7)).

Yield: 83%.

REFERENCE PRODUCTION EXAMPLE 6

Using 1.19 g of (4-(trifluoromethoxy)benzylidene)malononitrile, 20 ml of tetrahydrofuran, a catalytic amount of copper (I) iodide, and a solution of isopropyl magnesium bromide in tetrahydrofuran (prepared from 0.39 g of magnesium, 10 ml of tetrahydrofuran, and 2.36 g of isopropyl bromide), and according to the process described in REFERENCE PRODUCTION EXAMPLE 2, there was obtained 0.77 g of (1-(4-(trifluoromethoxy)phenyl)-2-methylpropyl)malononitrile (the intermediate (8)).

Yield: 55%.

REFERENCE PRODUCTION EXAMPLE 7

Using 1.19 g of (4-(trifluoromethoxy)benzylidene)malononitrile, 20 ml of tetrahydrofuran, a catalytic amount of copper (1) iodide, and 12.5 ml of a solution of methyl magnesium bromide in tetrahydrofuran (about 1 M, available from Tokyo Kasei Kogyo Co., Ltd), and according to the process described in REFERENCE PRODUCTION EXAMPLE 2, there was obtained 0.76 g of (1-(4-(trifluoromethoxy)phenyl)ethyl)malononitrile (the intermediate (10)).

Yield: 60%.

REFERENCE PRODUCTION EXAMPLE 8

First, 4.46 g of (3,4-dichlorobenzylidene)malononitrile was dissolved in 20 ml of tetrahydrofuran, and while stirring at room temperature, a suspension of 0.19 g of sodium borohydride in 5 ml of ethanol was added dropwise, followed by stirring at room temperature for 30 minutes. Then, 10% hydrochloride acid was added and the mixture was extracted with diethyl ether. The organic layer was successively washed with 10% hydrochloric acid, a saturated aqueous sodium chloride solution, dried over anhydrous magnesium sulfate, and then concentrated under reduced pressure. The residue was subjected to silica gel column chromatography to give 3.15 g of (3,4-dichlorobenzyl)malononitrile (the intermediate (12)).

Yield: 70%.

REFERENCE PRODUCTION EXAMPLE 9

Using 4.46 g of (2,4-dichlorobenzylidene)malononitrile, 20 ml of tetrahydrofuran, and a suspension of 0.19 g of sodium borohydride in 5 ml of ethanol, and according to the process described in Reference Production Example 8, there was obtained 3.10 g of (2,4-dichlorobenzyl)malononitrile (the intermediate (13)).

Yield: 69%.

REFERENCE PRODUCTION EXAMPLE 10

First, 10.0 g of 4-(trifluoromethylthio)benzaldehyde and 2.92 g of malononitrile were dissolved in 50 ml of 70% (w/w) aqueous ethanol, to which a catalytic amount of benzyltrimethylammonium hydroxide was added, and the mixture was stirred at room temperature overnight. Then, a saturated aqueous sodium chloride solution was added to the reaction mixture, which was extracted with ethyl acetate. The organic layer was washed with a saturated aqueous sodium chloride solution, dried over anhydrous magnesium sulfate, and then concentrated under reduced pressure. The residue was recrystallized with a solvent system consisting of t-butyl methyl ether and hexane to give 10.5 g of (4-(trifluoromethylthio)benzylidene)malononitrile.

Yield: 85%;

$^1$H-NMR (CDCl$_3$, TMS, δ (ppm)): 7.78 (1H, s), 7.79 (2H, d), 7.93 (2H, d).

Then, 8.00 g of (4-(trifluoromethylthio)benzylidene)malononitrile and 3.35 g of benzaldehyde were dissolved in 320 ml of ethanol, and while stirring at room temperature, 3.41 g of phenylenediamine was slowly added, and the mixture was stirred at room temperature for 5 hours. Then, the reaction mixture was concentrated, 300 ml of t-butyl methyl ether was added, and insoluble matters were filtered. The filtrate was concentrated and the resulting residue was subjected to silica gel chromatography to give 6.22 g of (4-(trifluoromethylthio)benzyl)malononitrile (the intermediate (14)).

Yield: 77%.

REFERENCE PRODUCTION EXAMPLE 11

First, 6.98 g of malononitrile, 681 mg of tetrabutylammonium bromide, and 10 g of 4-bromo-1,1,2-trifluoro-1-butene were mixed, and while stirring at 0° C. under an atmosphere of nitrogen, 5.92 g of potassium t-butoxide was slowly added. The mixture was further stirred at room temperature for 12 hours. Then, the reaction mixture was poured into water, followed by extraction with t-butyl methyl ether. The organic layer was washed with water, a saturated aqueous sodium chloride solution, dried over anhydrous magnesium sulfate, and then concentrated under reduced pressure. The residue was subjected to silica gel column chromatography to give 1.31 g of (3,4,4-trifluoro-3-butenyl)malononitrile (the intermediate (17)).

Yield: 26%.

REFERENCE PRODUCTION EXAMPLE 12

Using 4.00 g of (4-(trifluoromethoxy)benzylidene)malononitrile, 30 ml of tetrahydrofuran, 175 mg of copper (I) bromide dimethyl sulfide complex, and 26 ml of a solution (0.98 M) of vinyl magnesium bromide in tetrahydrofuran, and according to the process described in Reference Production Example 2, there was obtained 1.60 g of (1-(4-trifluoromethoxyphenyl))-2-propenylmalononitrile (the intermediate (18)).

REFERENCE PRODUCTION EXAMPLE 13

First, 27.6 g of malononitrile was dissolved in 50 ml of N,N-dimethylformamide, and 27.6 g of potassium carbonate was added at room temperature, followed by stirring for 1 hour. Then, a solution of 17.7 g of 1-bromo-3,3,3-trifluoropropane dissolved in 20 ml of N,N-dimethylformamide was added dropwise slowly, followed by stirring for 1 hour. Then, water was added to the reaction mixture, which was extracted with diethyl ether. The organic layer was successively washed with water, a saturated aqueous sodium chloride, dried over anhydrous magnesium sulfate, and then concentrated under reduced pressure. The residue was subjected to silica gel column chromatography to give 11.3 g of (3,3,3-trifluoropropyl)malononitrile (the intermediate (16)).

Yield: 68%.

REFERENCE PRODUCTION EXAMPLE 14

First, 20 ml of tetrahydrofuran was added dropwise slowly to the mixture of 0.50 g of dihydro tetrakis(triphenylphosphine)ruthenium and 3.00 g of (4-(trifluoromethyl)benzyl)malononitrile under an atmosphere of nitrogen , followed by stirring for 15 minutes. Then, 0.82 g of acrolein was added dropwise slowly, followed by stirring for 1 hour at room temperature and then the solvent was distilled away. The residue was subjected to silica gel column chromatography to give 1.58 g of 2-(2-formylethyl)-2-(4-(trifluoromethyl)benzyl)malononitrile (the intermediate (19)).

Yield: 42%.

REFERENCE PRODUCTION EXAMPLE 15

First, 0.01 g of sodium borohydride was added to the solution of 0.30 g of 2-(2-formylethyl)-2-(4-(trifluoromethyl)benzyl)malononitrile (the intermediate (19)) in ethanol at 0° C., followed by stirring for 5 hours at room temperature. Then, water was added to the reaction mixture, which was extracted with ethyl acetate. The organic layer was washed with a saturated aqueous sodium chloride, dried over anhydrous magnesium sulfate, and then concentrated under reduced pressure. The residue was subjected to silica gel column chromatography to give 0.19 g of 2-(3-hydroxypropyl)-2-(4-(trifluoromethyl)benzyl)malononitrile (the intermediate (20)).

Yield: 61%.

REFERENCE PRODUCTION EXAMPLE 16

Using 1.42 g of (2,4,6-trifluorobenzyliden)malononitrile, 50 ml of ethanol and 0.08 g of sodium borohydride, and according to the process described in the REFERENCE PRODUCTION EXAMPLE 3, there was obtained 1.29 g of (2,4,6-trifluorobenzyl)malononitrile (the intermediate (21)).

Yield: 90%.

REFERENCE PRODUCTION EXAMPLE 17

Using 10.0 g of (3,4-difluorobenzyliden)malononitrile, 200 ml of ethanol and 0.6 g of sodium borohydride, and according to the process described in the REFERENCE PRODUCTION EXAMPLE 3, there was obtained 8.05 g of (3,4-difluorobenzyl)malononitrile (the intermediate (23)).

Yield: 80%.

REFERENCE PRODUCTION EXAMPLE 18

Using 10.0 g of (2-chloro-4-fluorobenzyliden)malononitrile, 200 ml of ethanol and 0.6 g of sodium borohydride, and according to the process described in the REFERENCE PRODUCTION EXAMPLE 3, there was obtained 0.55 g of (2-chloro-4-fluorobenzyl)malononitrile (the intermediate (24)).

Yield: 53%.

REFERENCE PRODUCTION EXAMPLE 19

First, 0.93 g of 3-bromobenzaldehyde and 0.33 g of malononitrile were dissolved in 5 ml of ethanol, to which 1.5 ml of water was added, followed by stirring at room temperature for 4 hours. Then, after cooling at −5° C., a suspension of 57 mg of sodium borohydride in 3 ml of ethanol was added dropwise, followed by stirring at −5° C. for 30 minutes. 10% hydrochloride acid was added to the reaction mixture, which was extracted with ethyl acetate. The organic layer was washed with water, dried over anhydrous magnesium sulfate, and then concentrated under reduced pressure. The residue was subjected to silica gel column chromatography to give 0.94 g of (3-bromobenzyl)malononitrile (the intermediate (28)).

Yield: 83%.

REFERENCE PRODUCTION EXAMPLE 20

Using 1.02 g of 2-fluoro-4-bromobenzaldehyde, 0.33 g of malononitrile, 8 ml of ethanol, 1.5 ml of water and 57 mg of sodium borohydride, and according to the process described in the REFERENCE PRODUCTION EXAMPLE 19, there was obtained 1.21 g of (2-fluoro-4-bromobenzyl)malononitrile (the intermediate (29)).

Yield: 95%.

REFERENCE PRODUCTION EXAMPLE 21

Using 1.06 g of 3-(benzyloxy)benzaldehyde, 0.33 g of malononitrile, 8 ml of ethanol, 1.5 ml of water and 57 mg of sodium borohydride, and according to the process described in the REFERENCE PRODUCTION EXAMPLE 19, there was obtained 1.20 g of (3-(benzyloxy)benzyl)malononitrile (the intermediate (31)).

Yield: 92%.

REFERENCE PRODUCTION EXAMPLE 22

Using 1.0 g of (2,6-dichloro-4-(trifluoromethyl)benzyliden)malononitrile, 20 ml of ethanol and 0.03 g of sodium borohydride, and according to the process described in the REFERENCE PRODUCTION EXAMPLE 3, there was obtained 0.97 g of (2,6-dichloro-4-(trifluoromethyl)benzyl)malononitrile (the intermediate (32)).

Yield: 90%.

The intermediate compounds used in the production of the present compounds are shown below with the compound numbers and physical data.

Intermediate (1)
(4-Chlorobenzyl)malononitrile

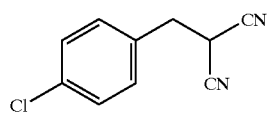

m.p.: 96.9° C.

Intermediate (2)
(1-(4-Chlorophenyl)-1-methylethyl)malononitrile

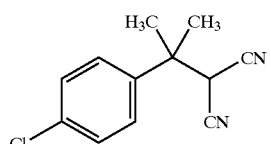

$n_D^{22.0}$: 1.5372.

Intermediate (3)
(1-(4-Chlorophenyl)-2-methylpropyl)malononitrile

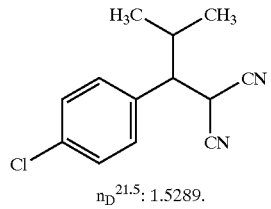

$n_D^{21.5}$: 1.5289.

Intermediate (4)
(4-(Trifluoromethyl)benzyl)malononitrile

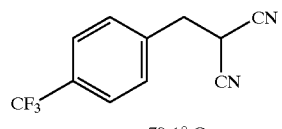

m.p.: 79.1° C.

Intermediate (5)
(4-Cyanobenzyl)malononitrile

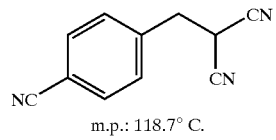

m.p.: 118.7° C.

Intermediate (6)
(1-(4-Chlorophenyl)ethyl)malononitrile

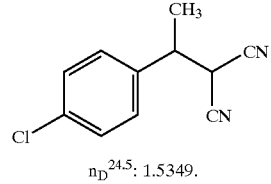

$n_D^{24.5}$: 1.5349.

Intermediate (7)
(4-(Trifluoromethoxy)benzyl)malononitrile

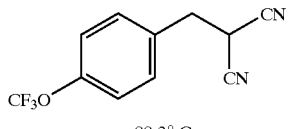

m.p.: 88.3° C.

Intermediate (8)
(1-(4-(Trifluoromethoxy)phenyl-2-methylpropyl)malononitrile

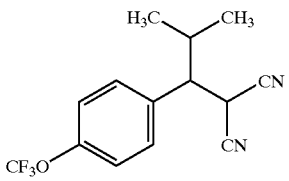

$^1$H-NMR (CDCl$_3$, TMS, δ (ppm)): 0.83 (3H, d), 1.16 (3H, d), 2.29–2.45 (1H, m), 2.87 (1H, dd), 4.18 (1H, d), 7.25–7.30 (2H, m), 7.38–7.42 (2H, m).

Intermediate (9)
(4-Bromobenzyl)malononitrile

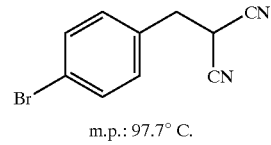

m.p.: 97.7° C.

-continued

Intermediate (10)

(1-(4-(Trifluoromethoxy)phenyl)ethyl)malononitrile

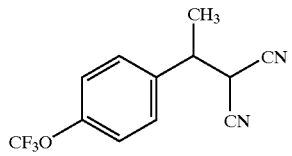

¹H-NMR (CDCl₃, TMS, δ (ppm)): 1.65 (3H, d), 3.49 (1H, dq), 3.85 (1H, d), 7.24–7.29 (2H, m), 7.38–7.42 (2H, m).

Intermediate (11)

(4-Fluorobenzyl)malononitrile

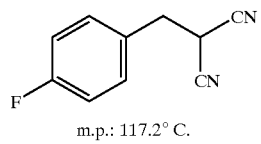

m.p.: 117.2° C.

Intermediate (12)

(3,4-Dichlorobenzyl)malononitrile

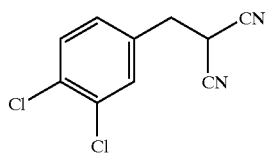

m.p.: 83.3° C.

Intermediate (13)

(2,4-Dichlorobenzyl)malononitrile

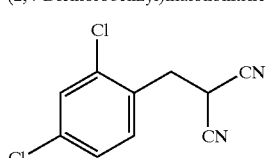

m.p.: 62.5° C.

Intermediate (14)

(4-(Trifluoromethylthio)benzyl)malononitrile

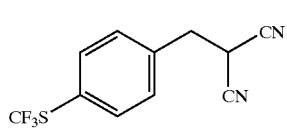

¹H-NMR (CDCl₃, TMS, δ (ppm)): 3.15 (2H, d), 3.95 (1H, t), 7.37 (2H, d), 7.70 (2H, d).

Intermediate (15)

Benzylmalononitrile

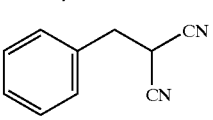

m.p.: 89.1° C.

Intermediate (16)

(3,3,3-Trifluoropropyl)malononitrile

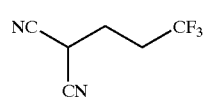

¹H-NMR (CDCl₃), TMS, δ (ppm)): 2.32–2.42 (2H, m), 2.43–2.52 (2H, m), 3.91 (1H, t).

-continued

Intermediate (17)

(3,4,4-Trifluoro-3-butenyl)malononitrile

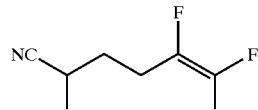

¹H-NMR (CDCl₃, TMS, δ (ppm)): 1.18–1.28 (1H, m), 2.27–2.34 (2H, m), 2.58–2.72 (2H, m), 3.88 (1H, t).

Intermediate (18)

(1-(4-Trifluoromethoxyphenyl))-2-propenyl)malononitrile

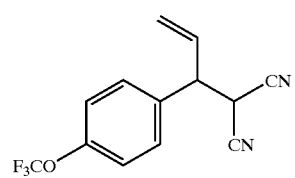

¹H-NMR (CDCl₃, TMS, δ (ppm)): 3.95–4.03 (2H, m), 5.40–5.53 (2H, m), 6.08–6.19 (1H, m), 7.28 (2H, d), 7.39 (2H, d).

Intermediate (19)

2-(2-formylethyl)-2-(4-trifluoromethyl)benzyl)malononitrile

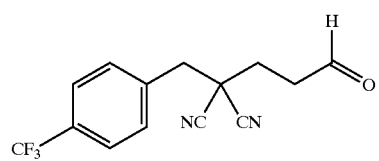

¹H-NMR (CDCl₃, TMS, δ (ppm)): 2.35(2H, t), 2.94(2H, t), 3.30(2H, s), 7.53(2H, d), 7.69(2H, d), 9.82(1H, s).

Intermediate (20)

2-(3-hydroxypropyl)-2-(4-trifluoromethyl)benzyl)malononitrile

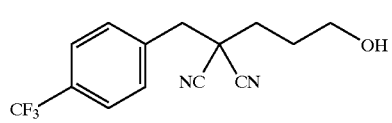

¹H-NMR (CDCl₃, TMS, δ (ppm)): 1.94–2.01(2H, m), 2.12–2.17(3H, m), 3.28(2H, s), 3.74(2H, t), 7.53(2H, d), 7.67(2H, d).

Intermediate (21)

(2,4,6-trifluorobenzyl)malononitrile

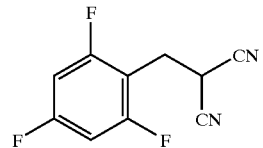

¹H-NMR (CDCl₃, TMS, δ (ppm)): 3.41(2H, d), 4.03(1H, t), 6.79(2H, dd).

Intermediate 22

(4-nitrobenzyl)malononitrile

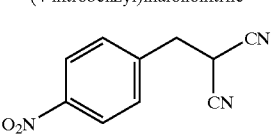

m.p.: 155.7° C.

-continued

Intermediate 23

(3,4-difluorobenzyl)malononitrile

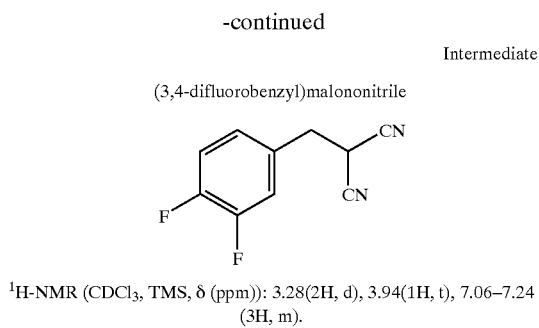

$^1$H-NMR (CDCl$_3$, TMS, δ (ppm)): 3.28(2H, d), 3.94(1H, t), 7.06–7.24 (3H, m).

Intermediate 24

(2-chloro-4-fluorobenzyl)malononitrile

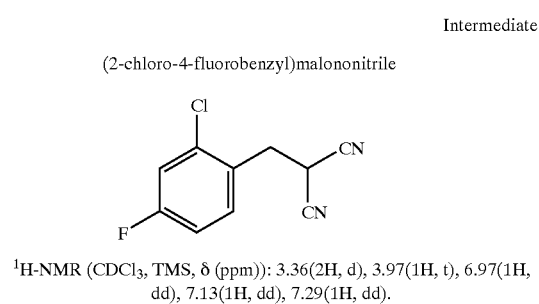

$^1$H-NMR (CDCl$_3$, TMS, δ (ppm)): 3.36(2H, d), 3.97(1H, t), 6.97(1H, dd), 7.13(1H, dd), 7.29(1H, dd).

Intermediate 25

(4-methoxybenzyl)malononitrile

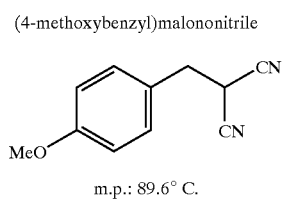

m.p.: 89.6° C.

Intermediate 26

(1-(4-trifluoromethyl)phenyl)ethyl)malononitrile

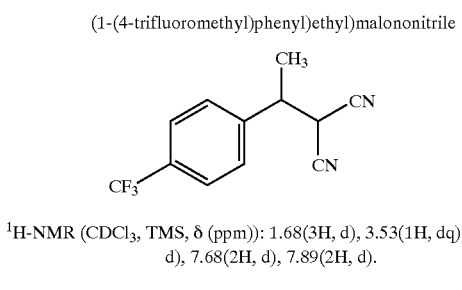

$^1$H-NMR (CDCl$_3$, TMS, δ (ppm)): 1.68(3H, d), 3.53(1H, dq), 3.89(1H, d), 7.68(2H, d), 7.89(2H, d).

Intermediate 27

(3-chlorobenzyl)malononitrile

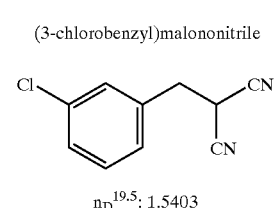

$n_D^{19.5}$: 1.5403

Intermediate 28

(3-bromobenzyl)malononitrile

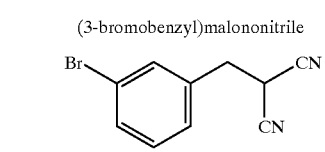

$^1$H-NMR (CDCl$_3$, TMS, δ (ppm)):3.26(2H, d), 3.93(1H, t), 7.26–7.30 (2H, m), 7.48(1H, bs), 7.51–7.55(1H, m).

Intermediate 29

(2-fluoro-4-bromobenzyl)malononitrile

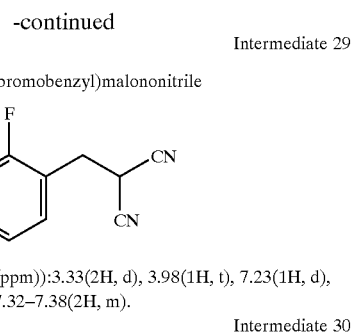

$^1$H-NMR (CDCl$_3$, TMS, δ (ppm)):3.33(2H, d), 3.98(1H, t), 7.23(1H, d), 7.32–7.38(2H, m).

Intermediate 30

(2-bromobenzyl)malononitrile

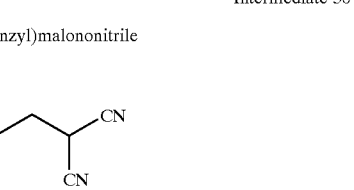

$^1$H-NMR (CDCl$_3$, TMS, δ (ppm)):3.45(2H, d), 4.15(1H, t), 7.23–7.29 (1H, m), 7.35–7.42(2H, m), 7.62(1H, d).

Intermediate 31

(3-(benzyloxy)benzyl)malononitrile

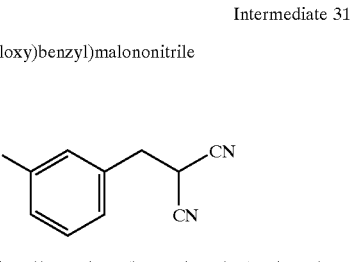

$^1$H-NMR (CDCl$_3$, TMS, δ (ppm)):3.24(2H, d), 3.88(1H, t), 5.07(2H, s), 6.89–6.99(3H, m), 7.28–7.45(6H, m).

Intermediate 32

(2,6-dichloro-4-(trifluoromethyl)benzyl)malononitrile

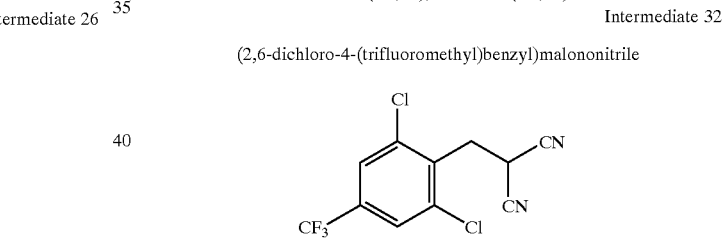

$^1$H-NMR (CDCl$_3$, TMS, δ (ppm)): 3.78(2H, d), 4.23(1H, t), 7.68(2H,s).

Specific examples of the present compounds are shown in Table 1 with the compound numbers.

TABLE 1

The compounds of formula (Y):

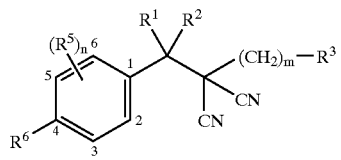

(Y)

| No. | R$^1$ | R$^2$ | m | R$^3$ | (R$^5$)$_n$ | R$^6$ |
|---|---|---|---|---|---|---|
| 1 | H | H | 1 | CCl=CH$_2$ | — | Cl |
| 2 | H | H | 1 | CCl=CH$_2$ | — | SCF$_3$ |
| 3 | H | H | 1 | CF$_3$ | — | H |
| 4 | H | H | 2 | CF=CF$_2$ | — | H |
| 5 | H | H | 1 | CF$_2$CF$_3$ | — | OCF$_3$ |
| 6 | H | H | 2 | CF$_3$ | — | C(=O)CH$_3$ |

TABLE 1-continued

The compounds of formula (Y):

| No. | R¹ | R² | m | R³ | (R⁵)ₙ | R⁶ |
|---|---|---|---|---|---|---|
| 7 | H | H | 2 | CF₃ | 2,6-Cl₂ | CF₃ |
| 8 | H | H | 2 | CF₂CF₃ | — | CF₃ |
| 9 | H | H | 2 | CF₃ | — | Br |
| 10 | H | H | 2 | CF₂CF₃ | — | OCF₃ |
| 11 | H | H | 2 | CHF₂ | — | CF₃ |
| 12 | H | H | 2 | CF₃ | — | H |
| 13 | H | H | 2 | CF₃ | — | SCF₃ |
| 14 | H | H | 2 | CH₂F | — | CF₃ |
| 15 | H | H | 2 | CF₃ | — | Cl |
| 16 | H | H | 2 | CF₃ | — | F |
| 17 | H | H | 2 | CF₃ | 2,6-F₂ | F |
| 18 | H | H | 2 | CF₃ | — | NO₂ |
| 19 | H | H | 2 | CF₃ | 3-F | F |
| 20 | H | H | 1 | CH=CCl₂ | — | Cl |
| 21 | H | H | 2 | CF₃ | 3-Cl | Cl |
| 22 | H | H | 2 | CF₃ | — | CN |
| 23 | H | H | 2 | CF₂CF₃ | — | Cl |
| 24 | H | H | 1 | CH₂F | — | Cl |
| 25 | H | H | 1 | CF₂CHF₂ | — | Cl |
| 26 | H | H | 2 | CF₃ | — | I |
| 27 | H | H | 2 | CF₃ | — | CH=CH₂ |
| 28 | H | H | 1 | CH=CCl₂ | — | OCF₃ |
| 29 | H | H | 1 | CH=CBr₂ | — | OCF₃ |
| 30 | H | H | 2 | CF₃ | 3-NO₂ | CH₃ |
| 31 | H | H | 2 | CF₃ | — | CH₂CH₃ |
| 32 | H | H | 2 | CF₃ | 3-OCH₃ | H |
| 33 | H | H | 2 | CF₃ | — | C(CH₃)₃ |
| 34 | H | H | 2 | CF₃ | — | SCH₃ |
| 35 | H | H | 2 | CF₃ | — | CH(CH₃)₂ |
| 36 | H | H | 2 | CF₃ | 3-CF₃ | H |
| 37 | H | H | 2 | CF₃ | 3-CH₃ | H |
| 38 | H | H | 2 | CF₃ | 2-Cl | NO₂ |
| 39 | H | H | 2 | CF₃ | 3-Cl | CF₃ |
| 40 | H | H | 2 | CF₃ | 2,3-(OCH₃)₂ | H |
| 41 | H | H | 2 | CF₃ | 2-Cl | CF₃ |
| 42 | H | CH₃ | 2 | CF₃ | — | Cl |
| 43 | H | H | 2 | CF₃ | — | CHBrCH₂Br |
| 44 | H | H | 2 | CF₃ | 2-Cl | F |
| 45 | H | H | 2 | CF₃ | 3-CH₃ | NO₂ |
| 46 | H | H | 1 | CH₂F | — | CN |
| 47 | H | H | 1 | CH₂F | — | NO₂ |
| 48 | H | H | 1 | CH₂=CFCF₃ | — | CF₃ |
| 49 | H | H | 2 | CF=CF₂ | — | OCF₃ |
| 50 | H | H | 2 | CF₃ | — | OCF₃ |
| 51 | H | H | 1 | CH₂F | — | Br |
| 52 | H | H | 1 | CH₂F | — | OCH₃ |
| 53 | H | CH₃ | 1 | CH₂F | — | Cl |
| 54 | H | H | 2 | CF=CF₂ | — | SCF₃ |
| 55 | H | H | 1 | CH=CCl₂ | — | CF₃ |
| 56 | H | H | 1 | CH=CCl₂ | — | CN |
| 57 | H | CH₃ | 2 | CF₃ | — | CF₃ |
| 58 | H | H | 2 | CF₃ | — | CH=CHBr |
| 59 | H | H | 1 | CH₂F | — | F |
| 60 | H | H | 1 | (E)-CH=CHCl | — | H |
| 61 | H | H | 1 | (Z)-CH=CHCl | — | H |
| 62 | H | H | 2 | CF=CF₂ | 2-Cl | CF₃ |
| 63 | H | H | 1 | CH₂Cl | 3-Cl | H |
| 64 | H | H | 1 | CH₂F | — | CF₃ |
| 65 | H | H | 1 | CH₂F | 3-Br | H |
| 66 | H | H | 2 | CF=CF₂ | 2,6-Cl₂ | CF₃ |
| 67 | H | H | 1 | CH₂F | 2-F | Br |
| 68 | H | H | 2 | CF=CF₂ | — | CN |
| 69 | H | H | 1 | CH₂F | 2-Br | H |
| 70 | H | H | 2 | CF₃ | 2-F | F |
| 71 | H | H | 2 | CF₃ | 3,5-F₂ | H |
| 72 | H | H | 1 | CF₃ | — | CF₃ |
| 73 | H | H | 2 | CF=CF₂ | — | CF₃ |
| 74 | H | H | 2 | CF₃ | — | CF₃ |
| 75 | H | H | 2 | CF₃ | 2-F | H |
| 76 | H | H | 1 | CF₂CF₃ | — | CF₃ |
| 77 | H | H | 1 | CF₂CF₂CF₃ | — | CF₃ |
| 78 | H | H | 3 | CF₃ | — | CF₃ |
| 79 | H | H | 2 | CF₃ | 3-F | H |
| 80 | H | H | 2 | CF₃ | 2,3,5,6-F₄ | F |
| 81 | H | H | 2 | CF₃ | 2-Cl | H |
| 82 | H | H | 2 | CF₃ | 3-Cl | H |
| 83 | H | H | 2 | CF₃ | 2-Cl | Cl |
| 84 | H | H | 2 | CF₃ | — | CH₃ |
| 85 | H | H | 2 | CH₂Cl | — | CF₃ |
| 86 | H | H | 1 | CH(CH₃)CH₂Cl | — | CF₃ |
| 87 | H | H | 3 | CH₂Cl | — | CF₃ |
| 88 | H | H | 2 | CF₃ | 3-OCH₂Ph | H |
| 89 | H | H | 2 | CF₃ | — | OCH₃ |
| 90 | H | H | 2 | CF₃ | 3-F | CF₃ |
| 91 | H | CH₃ | 2 | CF₃ | 3-F | CF₃ |
| 92 | H | H | 2 | CF₃ | 3-CH₃ | CN |
| 93 | H | H | 2 | CF₃ | 3-CF₃ | Cl |
| 94 | H | CH₃ | 2 | CF₃ | 3-CF₃ | Cl |
| 95 | H | H | 2 | CF₃ | 3-Cl | NO₂ |
| 96 | H | H | 2 | CF₃ | 3-F | NO₂ |
| 97 | H | H | 2 | CF₃ | 3-F | CN |
| 98 | H | CH₃ | 2 | CF₃ | 3-F | CN |
| 99 | H | H | 2 | CF₃ | 3,5-F₂ | CF₃ |
| 100 | H | H | 2 | CF₃ | 3-Cl | F |
| 101 | H | CH₃ | 2 | CF₃ | 3-Cl | F |
| 102 | H | H | 2 | CF₃ | 3-Cl | F |
| 103 | H | CH₃ | 2 | CF₃ | 3-F | Cl |
| 104 | H | H | 2 | CF₃ | 3,5-Cl₂ | Cl |
| 105 | H | H | 2 | CF₃ | 3,5-F₂ | F |
| 106 | H | CH₃ | 2 | CF₃ | — | OCF₃ |
| 107 | H | CH₃ | 2 | CF₃ | — | SCF₃ |
| 108 | H | H | 3 | CF₃ | — | OCF₃ |
| 109 | H | H | 3 | CF₃ | — | SCF₃ |
| 110 | H | H | 3 | CF₃ | — | NO₂ |
| 111 | H | H | 3 | CF₃ | — | CN |
| 112 | H | CH₃ | 3 | CF₃ | — | CN |
| 113 | H | H | 3 | CF₃ | — | Cl |
| 114 | H | CH₃ | 3 | CF₃ | — | Cl |
| 115 | H | H | 3 | CF₃ | — | F |
| 116 | H | H | 3 | CF₃ | 3-Cl | CF₃ |
| 117 | H | CH₃ | 3 | CF₃ | 3-Cl | CF₃ |
| 118 | H | H | 3 | CF₃ | 3-F | CF₃ |
| 119 | H | CH₃ | 3 | CF₃ | 3-F | CF₃ |
| 120 | H | H | 3 | CF₃ | 3-Cl | F |
| 121 | H | CH₃ | 3 | CF₃ | 3-Cl | F |
| 122 | H | H | 3 | CF₃ | 3-Cl | CN |
| 123 | H | H | 3 | CF₃ | 3-Cl | Cl |
| 124 | H | CH₃ | 3 | CF₃ | 3-Cl | Cl |
| 125 | H | H | 3 | CF₃ | 3-F | F |
| 126 | H | CH₃ | 3 | CF₃ | 3-F | F |
| 127 | H | H | 3 | CF₃ | 3-CF₃ | H |
| 128 | H | H | 2 | CF₂CF₃ | — | OCF₃ |
| 129 | H | H | 2 | CF₂CF₃ | — | SCF₃ |
| 130 | H | H | 2 | CF₂CF₃ | — | NO₂ |
| 131 | H | H | 2 | CF₂CF₃ | — | CN |
| 132 | H | CH₃ | 2 | CF₂CF₃ | — | CN |
| 133 | H | H | 2 | CF₂CF₃ | — | Cl |
| 134 | H | CH₃ | 2 | CF₂CF₃ | — | Cl |
| 135 | H | H | 2 | CF₂CF₃ | — | F |
| 136 | H | H | 2 | CF₂CF₃ | 3-Cl | CF₃ |
| 137 | H | CH₃ | 2 | CF₂CF₃ | 3-Cl | CF₃ |
| 138 | H | H | 2 | CF₂CF₃ | 3-F | CF₃ |

TABLE 1-continued

The compounds of formula (Y):

$$\text{(Y)}$$

| No. | R¹ | R² | m | R³ | (R⁵)ₙ | R⁶ |
|---|---|---|---|---|---|---|
| 139 | H | CH₃ | 2 | CF₂CF₃ | 3-F | CF₃ |
| 140 | H | H | 2 | CF₂CF₃ | 3-Cl | F |
| 141 | H | CH₃ | 2 | CF₂CF₃ | 3-Cl | F |
| 142 | H | H | 2 | CF₂CF₃ | 3-Cl | CN |
| 143 | H | H | 2 | CF₂CF₃ | 3-Cl | Cl |
| 144 | H | CH₃ | 2 | CF₂CF₃ | 3-Cl | Cl |
| 145 | H | H | 2 | CF₂CF₃ | 3-F | F |
| 146 | H | CH₃ | 2 | CF₂CF₃ | 3-F | F |
| 147 | H | H | 2 | CF₂CF₃ | 3-CF₃ | H |
| 148 | H | CH₃ | 2 | CF₃ | 3-Cl | Cl |
| 149 | H | CH₃ | 2 | CF₃ | 3-F | F |
| 150 | H | CH₃ | 2 | CF₃ | 3-Cl | CF₃ |
| 151 | H | CH₃ | 2 | CF₃ | 3-CF₃ | Cl |
| 152 | H | H | 2 | CF₃ | 3-CF₃ | Cl |
| 153 | H | CH₃ | 2 | CF₃ | 3-CF₃ | H |
| 154 | H | H | 1 | CH=CF₂ | — | CF₃ |
| 155 | H | H | 1 | CH=CF₂ | — | Cl |
| 156 | H | CH₃ | 1 | CH=CF₂ | — | F |
| 157 | H | H | 1 | CH=CF₂ | — | CN |
| 158 | H | H | 1 | CH=CF₂ | — | NO₂ |
| 159 | H | CH(CH₃)₂ | 1 | CH=CF₂ | — | SCF₃ |
| 160 | H | H | 1 | CH=CF₂ | — | OCF₃ |
| 161 | H | H | 1 | CH=CF₂ | 3-Cl | Cl |
| 162 | H | H | 1 | CH=CF₂ | 3-Cl | F |
| 163 | H | H | 1 | CH=CF₂ | 3-F | F |
| 164 | H | H | 1 | CH=CF₂ | 3-Cl | CF₃ |
| 165 | H | H | 1 | CH=CF₂ | 3-F | CF₃ |
| 166 | H | H | 2 | CH=CF₂ | — | CF₃ |
| 167 | H | H | 2 | CH=CF₂ | — | Cl |
| 168 | H | H | 2 | CH=CF₂ | — | F |
| 169 | H | H | 2 | CH=CF₂ | — | CN |
| 170 | H | CH₃ | 2 | CHCF₂ | — | NO₂ |
| 171 | H | H | 2 | CHCF₂ | — | SCF₃ |
| 172 | H | CH(CH₃)₂ | CH=CF₂ | — | OCF₃ | |
| 173 | H | H | 2 | CH=CF₂ | 3-Cl | Cl |
| 174 | H | H | 2 | CH=CF₂ | 3-Cl | F |
| 175 | H | H | 2 | CH=CF₂ | 3-F | F |
| 176 | H | H | 2 | CH=CF₂ | 3-Cl | CF₃ |
| 177 | H | H | 2 | CH=CF₂ | 3-F | CF₃ |
| 178 | H | H | 2 | CF₂CH₃ | — | CF₃ |
| 179 | H | H | 2 | CF₂CH₃ | — | Cl |
| 180 | H | H | 2 | CF₂CH₃ | — | F |
| 181 | H | H | 2 | CF₂CH₃ | — | CN |
| 182 | H | H | 2 | CF₂CH₃ | — | NO₂ |
| 183 | H | CH₃ | 2 | CF₂CH₃ | — | SCF₃ |
| 184 | H | CH(CH₃)₂ | CF₂CH₃ | — | OCF₃ | |
| 185 | H | H | 2 | CF₂CH₃ | 3-Cl | Cl |
| 186 | H | H | 2 | CF₂CH₃ | 3-Cl | F |
| 187 | H | H | 2 | CF₂CH₃ | 3-F | F |
| 188 | H | H | 2 | CF₂CH₃ | 3-Cl | CF₃ |
| 189 | H | H | 2 | CF₂CH₃ | 3-F | CF₃ |
| 190 | H | H | 2 | C(CF₃)=CH₂ | — | CF₃ |
| 191 | H | H | 2 | C(CF₃)=CH₂ | — | Cl |
| 192 | H | H | 2 | C(CF₃)=CH₂ | — | F |
| 193 | H | H | 2 | C(CF₃)=CH₂ | — | CN |
| 194 | H | CH(CH₃)₂ | C(CF₃)=CH₂ | — | NO₂ | |
| 195 | H | H | 2 | C(CF₃)=CH₂ | — | SCF₃ |
| 196 | H | CH₃ | 2 | C(CF₃)=CH₂ | — | OCF₃ |
| 197 | H | H | 2 | C(CF₃)=CH₂ | 3-Cl | Cl |
| 198 | H | H | 2 | C(CF₃)=CH₂ | 3-Cl | F |
| 199 | H | H | 2 | C(CF₃)=CH₂ | 3-F | F |
| 200 | H | H | 2 | C(CF₃)=CH₂ | 3-Cl | CF₃ |
| 201 | H | H | 2 | C(CF₃)=CH₂ | 3-F | CF₃ |
| 202 | H | H | 1 | C(CF₃)=CH₂ | — | CF₃ |
| 203 | H | H | 1 | C(CF₃)=CH₂ | — | Cl |
| 204 | H | H | 1 | C(CF₃)=CH₂ | — | F |
| 205 | H | H | 1 | C(CF₃)=CH₂ | — | CN |
| 206 | H | H | 1 | C(CF₃)=CH₂ | — | NO₂ |
| 207 | H | H | 1 | C(CF₃)=CH₂ | — | SCF₃ |
| 208 | H | H | 1 | C(CF₃)=CH₂ | — | OCF₃ |
| 209 | H | H | 1 | C(CF₃)=CH₂ | 3-Cl | Cl |
| 210 | H | H | 1 | C(CF₃)=CH₂ | 3-Cl | F |
| 211 | H | H | 1 | C(CF₃)=CH₂ | 3-F | F |
| 212 | H | H | 1 | C(CF₃)=CH₂ | 3-Cl | CF₃ |
| 213 | H | H | 1 | C(CF₃)=CH₂ | 3-F | CF₃ |
| 214 | H | H | 2 | CH₂Cl | — | CF₃ |
| 215 | H | H | 2 | CH₂Cl | — | CN |
| 216 | H | H | 2 | CH₂Cl | 3-Cl | Cl |
| 217 | H | H | 3 | CH₂F | — | NO₂ |
| 218 | H | H | 3 | CH₂F | 3-Cl | Cl |
| 219 | H | H | 3 | CH₂F | 3-Cl | F |
| 220 | H | H | 3 | CH₂F | 3-Cl | CF₃ |
| 221 | H | OCH₃ | 2 | CF₃ | — | CF₃ |
| 222 | H | OCH(CH₃)₂ | 2 | CF₃ | — | CN |
| 223 | H | CN | 2 | CF₃ | — | Cl |

The following will describe some formulation examples wherein parts represent parts by weight. The present compounds are designated by their compound numbers shown in Table 1.

FORMULATION EXAMPLE 1

Nine parts of each of the present compounds (1) to (87) is dissolved in 37.5 parts of xylene and 37.5 parts of dimethylformamide, and 10 parts of polyoxyethylene styryl phenyl ether and 6 parts of calcium dodecylbenzene-sulfonate are added thereto, followed by well stirring and mixing, to give an emulsifiable concentrate for each compound.

FORMULATION EXAMPLE 2

To 40 parts of each of the present compounds (1) to (87) is added 5 parts of Solpol® 5060 (Toho Chemical Industry Co., Ltd.), followed by well mixing, and 32 parts of Carplex® #80 (synthetic hydrated silicone oxide fine powder; Shionogi & Co., Ltd.) and 23 parts of 300 mesh diatomaceous earth are added, which is mixed with a mixer to give a wettable powder for each compound.

FORMULATION EXAMPLE 3

To 3 parts of each of the present compounds (1) to (87) are added 5 parts of synthetic hydrated silicon oxide fine powder, 5 parts of sodium dodecylbenzenesulfonate, 30 parts of bentonite, and 57 parts of clay, followed by well stirring and mixing, and an appropriate amount of water is added to this mixture, followed by further stirring, granulation with a granulator, and air drying, to give a granule for each compound.

FORMULATION EXAMPLE 4

First, 4.5 parts of each of the present compounds (1) to (87), 1 part of synthetic hydrated silicon oxide fine powder, 1 part of Doriresu B (Sankyo Co., Ltd.) as a flocculant, and 7 parts of clay are well mixed with a mortar, followed by stirring and mixing with a mixer. To the resulting mixture is added 86.5 parts of cut clay, followed by well stirring and mixing, to give a dust for each compound.

FORMULATION EXAMPLE 5

Ten parts of each of the present compounds (1) to (87), 35 parts of white carbon containing 50 parts of polyoxyethylene alkyl ether sulfate ammonium salt, and 55 parts of water are mixed and pulverized by the wet grinding method to give a formulation for each compound.

FORMULATION EXAMPLE 6

First, 0.5 parts of each of the present compounds (1) to (87) is dissolved in 10 parts of dichloromethane, which is mixed with 89.5 parts of ISOPAR ®M (isoparaffin; Exxon Chemical Co.) to give an oil formulation for each compound.

FORMULATION EXAMPLE 7

First, 0.1 parts of the present compounds (1) to (79) and 49.9 parts of NEO-CHIOZOL (Chuo Kasei K.K.) are put into an aerosol can, to which an aerosol valve is attached. Then, 25 parts of dimethyl ether and 25 parts of LPG are filled in the aerosol can, followed by shaking and attachment of an actuator, to give an oil-based aerosol.

FORMULATION EXAMPLE 8

First, 0.6 parts of each of the present compounds (1) to (79), 0.01 parts of BHT, 5 parts of xylene, 3.39 parts of deodorized kerosine, and 1 part of an emulsifier (Atmos 300; Atmos Chemical Co.) are mixed to become a solution. Then, this solution and 50 parts of distilled water are filled in an aerosol can, to which a valve part is attached, and 40 parts of a propellant (LPG) is filled under pressure through the valve in the aerosol can to give a water-based aerosol.

The following test example will demonstrate that the present compounds are useful as the active ingredients of pesticide compositions. The present compounds are designated by their compound numbers shown in Table 1.

TEST EXAMPLE 1

Pesticidal Test against *Nilaparvata lugens*

Each formulation of the compound 2, 5, 7, 8, 9, 10, 11, 12, 13, 15, 16, 19, 21, 22, 23, 24, 25, 26, 27, 30, 31, 32, 33, 34, 35, 36, 37, 38, 39, 40, 41, 43, 44, 46, 49, 50, 53, 55, 57, 58, 59, 61, 64, 66, 68, 72, 73, 74, 76, 78 and 89 obtained according to Formulation Example 5 was diluted with water so that the active ingredient concentration came to 500 ppm to prepare a test liquid for each compound. And each formulation of the compound 17 and 76 obtained according to Formulation Example 5 was diluted with water so that the active ingredient concentration came to 200 ppm to prepare a test liquid for each compound.

Fifty grams of molding Bonsoru 2 (available from Sumitomo Chemical Co., Ltd.) was put into a polyethylene cup, and 10 to 15 seeds of rice were planted in the polyethylene cup. Then rice plants were grown until the second foliage leaves developed and then cut into the same height of 5 cm. The test liquid, which had been prepared as described above, was sprayed at the rate of 20 ml/cup onto these rice plants. After the test liquid sprayed onto the rice plants were dried, the polyethylene cup with the rice plants was placed in a large polyethylene cup and 30 first-instar larvae of *Nilaparvata lugens* (brown planthopper) were set free in the large polyethylene cup, which was then kept covered and left in a greenhouse at 25° C. On the 6th day after the release of larvae of *Nilaparvata lugens*, the number of parasitic *Nilaparvata lugens* on the rice plants was examined.

As a result, in the treatment with each of the compounds described above, the number of parasitic pests on the 6th day after the treatment was not greater than 3.

TEST EXAMPLE 2

Pesticidal Test against *Nilaparvata lugens*

Each formulation of the compound 5, 8, 9, 10, 11, 12, 13, 15, 16, 18, 19, 21, 22, 23, 27, 31, 33, 34, 36, 37, 39, 40, 41, 44, 49, 50, 57, 68, 72, 73, 74, 77 and 89 obtained according to Formulation Example 5 was diluted with water so that the active ingredient concentration came to 45.5 ppm to prepare a test liquid for each compound. And each formulation of the compound 17, 26 and 76 obtained according to Formulation Example 5 was diluted with water so that the active ingredient concentration came to 18.2 ppm to prepare a test liquid for each compound.

Fifty grams of molding Bonsoru 2 (available from Sumitomo Chemical Co., Ltd.) was put into a polyethylene cup having five holes of 5 mm, and 10 to 15 seeds of rice were planted in the polyethylene cup. Then rice plants were grown until the second foliage leaves developed and the polyethylene cup with the rice plants was placed in a large polyethylene cup containing 55 ml of the test liquid, which had been prepared as described above, was poured. The rice plants were left in a greenhouse at 25° C. for 6 days and then cut into the same height of 5 cm. Thirty first-instar larvae of *Nilaparvata lugens* (brown planthopper) were set free in the large polyethylene cup, which was then kept covered and left in a greenhouse at 25° C. On the 6th day after the release of larvae of *Nilaparvata lugens*, the number of parasitic *Nilaparvata lugens* on the rice plants was examined.

As a result, in the treatment with each of the compounds described above, the number of parasitic pests on the 6th day after the treatment was not greater than 3.

TEST EXAMPLE 3

Pesticidal Test against *Aphis gossypii*

Each formulation of the compound 8, 9, 10, 11, 13, 15, 16, 18, 19, 21, 22, 23, 24, 34, 39, 41, 46, 47, 50, 51, 52, 53, 57, 59, 64, 67, 69 and 74 obtained according to Formulation Example 5 was diluted with water so that the active ingredient concentration came to 500 ppm to prepare a test liquid for each compound.

The seeds of cucumber were planted in a polyethylene cup of 90 ml volume filled with Molding Aisai 1 (available from Katakura Chikkarin Co., Ltd,) and grown until their first foliage leaves developed. About 30 *Aphis gossypii* (cotton aphid) were made parasitic on the cucumber plants, which was then left for 24 hours. The test liquid was sprayed at the rate of 20 ml/cup onto the cucumber plants. After the test liquid sprayed onto the plants were dried, the polyethylene cup with the cucumber plants was placed in a large polyethylene cup, which was then kept covered and left in a greenhouse at 25° C. On the 6th day after the application, the number of Aphis gossypii was examined.

As a result, in the treatment with each of the compounds described above, the number of survived pests on the 6th day after the treatment was not greater than 3.

TEST EXAMPLE 4

Pesticidal Test against Eysarcoris lewisi

Each formulation of the compound 8, 9, 10, 11, 14, 21, 22, 23, 39, 50, 74 and 76 obtained according to Formulation Example 1 was diluted with water so that the active ingredient concentration came to 100 ppm to prepare a test liquid for each compound.

Then, 3 to 5 seeds of peanut were immersed in the test liquid, which had been prepared as described above, for 1 minute. After the test liquid treated the seeds of peanut was dried with a paper towel, a filter paper moistened with 1 ml of water was placed on a bottom of polyethylene cup and then the seeds of peanut was placed on it. Six to eight adults of Eysarcoris lewisi were set free in the polyethylene cup, which was then kept covered and left in a greenhouse at 25° C. On the 7th day after the release of Eysarcoris lewisi, the number of dead pests and moribund pests was examined.

As a result, in the treatment with each of the compounds described above, the rate of dead or moribund pests was 100%.

TEST EXAMPLE 5

Pesticidal Test against Leptinotarsa decemlineata

Each formulation of the compound 5, 8, 10, 15, 21, 50, 74, 76 and 78 obtained according to Formulation Example 1 was diluted with water so that the active ingredient concentration came to 1.6 ppm to prepare a test liquid for each compound.

A leaf of eggplant was immersed in the test liquid, which had been prepared as described above, for 1 minute. After the test liquid treated the leaf of eggplant was dried with a paper towel, the leaf of eggplant was placed in a polyethylene cup of 3 cm in diameter. One second-instar larvae of Leptinotarsa decemlineata (Colorado potato beetle) were set free in the polyethylene cup, which was then kept covered and left in a greenhouse at 25° C. This test was done ten times for one compound. On the 5th day after the release of Leptinotarsa decemlineata, the number of dead pests and moribund pests was examined.

As a result, in the treatment with each of the compounds described above, the rate of dead or moribund pests was greater than 80%.

TEST EXAMPLE 6

Pesticidal Test against Musca domestica

Each formulation of the compound 4, 5, 7, 8, 9, 10, 11, 12, 13, 14, 15, 16, 18, 19, 21, 22, 23, 26, 27, 31, 33, 34, 35, 36, 39, 42, 44, 45, 46, 49, 50, 53, 54, 57, 59, 71, 72, 73, 74, 76, 77, 78, 79, 88 and 89 obtained according to Formulation Example 5 was diluted with water so that the active ingredient concentration came to 500 ppm to prepare a test liquid for each compound.

On the bottom of a polyethylene cup of 5.5 cm in diameter was placed a filter paper on the same size, to which the test liquid had been prepared as described above, was added dropwise in an amount of 0.7 ml, and 30 mg of sucrose as a bait was placed on it. Ten female adults of Musca domestics (house fly) were set free in the polyethylene cup, which was then kept covered. After 24 hours, their survival was examined to determine the mortality.

As a result, in the treatment with each of the compounds described above, it was exhibited the mortality of 100%.

TEST EXAMPLE 7

Pesticidal Test against Blattalla germanica

Each formulation of the compound 4, 5, 6, 7, 8, 9, 10, 11, 13, 15,16, 17, 19, 21, 22, 23, 26, 31, 34, 36, 39, 42, 44, 49, 50, 54, 57, 62, 64, 70, 72, 73, 74, 77 and 80 obtained according to Formulation Example 5 was diluted with water so that the active ingredient concentration came to 500 ppm to prepare a test liquid for each compound.

On the bottom of a polyethylene cup of 5.5 cm in diameter was placed a filter paper on the same size, to which the test liquid had been prepared as described above, was added dropwise in an amount of 0.7 ml, and 30 mg of sucrose as a bait was placed on it. Two male adults of Blattalla germanica (German cockroach) were set free in the polyethylene cup, which was then kept covered. After 6 days, their survival was examined to determine the mortality.

As a result, in the treatment with each of the compounds described above, it was exhibited the mortality of 100%.

TEST EXAMPLE 8

Pesticidal Test against Cullex pipiens pallens

Each formulation of the compound 1, 2, 4, 5, 6, 7, 8, 9, 10, 11, 12, 13, 14, 15, 16, 17, 18, 19, 20, 21, 22, 23, 25, 26, 27, 28, 29, 30, 31, 32, 33, 34, 35, 36, 37, 38, 39, 40, 42, 43, 44, 46, 49, 50, 54, 55, 56, 57, 59, 62, 64, 66, 68, 70, 71, 72, 73, 74, 75, 76, 77, 78, 79, 80, 81, 82, 83, 84, 85, 86, 87, 88 and 89 obtained according to Formulation Example 5 was diluted with water so that the active ingredient concentration came to 500 ppm to prepare a test liquid for each compound.

In 100 ml of ion-exchanged water, the test liquid had been prepared as described above, was added dropwise in an amount of 0.7 ml. The concentration of active ingredient was 3.5 ppm. Twenty final-instar larvae of Cullex pipiens pallens (common mosquito) were set free in the solution. After 1 days, their survival was examined to determine the mortality.

As a result, in the treatment with each of the compounds described above, it was exhibited the mortality of 100%.

TEST EXAMPLE 9

Pesticidal Test against Ctenocephalides felis

Each of the compound 8, 15, 19, 21 and 34 was dissolved in acetone to give a 0.2 ml solution of 0.114% w/w, which was uniformly treated on a filter paper having 3.8cm in diameter, and air-dried. The amount of active ingredient was 200 mg/m$^2$. The filter paper was filled in a lid of a 200 ml glass bottle. Twenty adult Ctenocephalides felis (cat flea) were released in the glass bottle, which was followed by covering with the lid. The glass bottle was upset for making the fleas contact with the filter paper. After 24 hours, the mortality was examined.

As a result, in the treatment with each of the compounds described above, it was exhibited the mortality of 100%.

INDUSTRIAL APPLICABILITY

The present invention makes it possible to effectively control pests such as insect pests, acarine pests, and nematode pests.

What is claimed is:

1. A malononitrile compound of formula (Y):

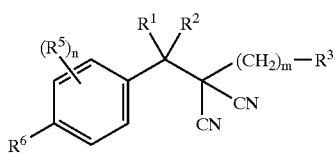

wherein $R^1$ and $R^2$ are the same or different and independently $C_1$–$C_5$ (halo)alkyl, $C_1$–$C_5$ (halo)alkyloxy, $C_2$–$C_5$ (halo)alkenyl, $C_2$–$C_5$ (halo)alkynyl, hydrogen, or cyano;
$R^3$ is $C_1$–$C_3$ haloalkyl, $C_2$–$C_4$ haloalkenyl, or $C_2$–$C_4$ haloalkynyl;
m is an integer of 1 to 3;
$R^5$ is halogen, cyano, nitro, $C_1$–$C_4$ (halo)alkyl, $C_2$–$C_4$ (halo)alkenyl, $C_2$–$C_4$ (halo)alkynyl, $C_1$–$C_4$ (halo)alkyloxy, $C_1$–$C_4$ (halo)alkylthio, $C_1$–$C_4$ (halo)alkylsulfinyl, $C_1$–$C_4$ (halo)alkylsulfonyl, $C_1$–$C_4$ (halo)alkylcarbonyl, $C_1$–$C_4$ (halo)alkyloxycarbonyl, $C_1$–$C_4$ (halo)alkylcarbonyloxy, benzyloxy, phenyloxy, or phenylthio, in which the phenyloxy and phenylthio groups may optionally be substituted with halogen or $C_1$–$C_3$ alkyl;
n is an integer of 0 to 4;
$R^6$ is hydrogen, halogen, cyano, nitro, $C_1$–$C_4$ (halo)alkyl, $C_2$–$C_4$ (halo)alkenyl, $C_2$–$C_4$ (halo)alkynyl, $C_1$–$C_4$ (halo)alkyloxy, $C_1$–$C_4$ (halo)alkylthio, $C_1$–$C_4$ (halo)alkylsulfinyl, $C_1$–$C_4$ (halo)alkylsulfonyl, $C_1$–$C_4$ (halo)alkylcarbonyl, $C_1$–$C_4$ (halo)alkyloxycarbonyl, $C_1$–$C_4$ (halo)alkylcarbonyloxy, benzyloxy, phenyloxy, or phenylthio, in which the phenyloxy and phenylthio groups may optionally be substituted with halogen or $C_1$–$C_3$ alkyl with the proviso that when n is 2 or more, then $R^5$'s are the same or different from each other.

2. The malononitrile compound according to claim 1, wherein $R^6$ is halogen, cyano, nitro, $C_1$–$C_4$ haloalkyl, $C_1$–$C_4$ haloalkyloxy or $C_1$–$C_4$ haloalkylthio.

3. The malononitrile compound according to claim 1, wherein $R^1$ and $R^2$ are both hydrogen.

4. The malononitrile compound according to claim 1, wherein $R^3$ is fluoromethyl, trifluoromethyl, or 1,2,2-trifluoroethenyl, and m is 1 or 2.

5. The malononitrile compound according to claim 1, wherein $R^1$ and $R^2$ are the same or different and independently $C_1$–$C_3$ (halo)alkyl, $C_1$–$C_3$ (halo)alkyloxy, $C_2$–$C_4$ (halo)alkenyl, $C_2$–$C_4$ (halo)alkynyl, hydrogen, or cyano; $R^5$ and $R^6$ are the same or different and independently halogen, cyano, nitro, $C_1$–$C_3$ haloalkyl, $C_1$–$C_3$ haloalkyloxy, $C_1$–$C_3$ (halo)alkylthio, $C_1$–$C_3$ (halo)alkylsulfinyl, $C_1$–$C_3$ (halo)alkylsulfonyl, $C_1$–$C_3$ (halo)alkylcarbonyl, or $C_1$–$C_3$ haloalkyloxycarbonyl.

6. The malononitrile compound according to claim 5, wherein $R^3$ is $C_1$–$C_5$ haloalkyl and m is 1.

7. A pesticide composition comprising the malononitrile compound of claim 1 as active ingredient and a carrier.

8. A pest controlling method comprising applying a pesticidally effective amount of the malononitrile compound of claim 1 to pests or habitats of pests.

9. The pest controlling method according to claim 8, wherein the pests are insect pests.

* * * * *